(12) United States Patent
Crystal et al.

(10) Patent No.: US 10,093,947 B2
(45) Date of Patent: Oct. 9, 2018

(54) AAV-DIRECTED PERSISTENT EXPRESSION OF AN ANTI-NICOTINE ANTIBODY GENE FOR SMOKING CESSATION

(71) Applicant: Cornell University, Ithaca, NY (US)

(72) Inventors: Ronald G. Crystal, New York, NY (US); Martin J. Hicks, New York, NY (US); Jonathan B. Rosenberg, Cranbury, NJ (US); Bishnu P. De, New Hyde Park, NY (US); Stephen M. Kaminsky, Bronx, NY (US); Robin L. Davisson, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 14/381,534

(22) PCT Filed: Feb. 25, 2013

(86) PCT No.: PCT/US2013/027619
§ 371 (c)(1),
(2) Date: Aug. 27, 2014

(87) PCT Pub. No.: WO2013/130393
PCT Pub. Date: Sep. 6, 2013

(65) Prior Publication Data
US 2015/0056251 A1 Feb. 26, 2015

Related U.S. Application Data

(60) Provisional application No. 61/604,203, filed on Feb. 28, 2012.

(51) Int. Cl.
| | |
|---|---|
| *C12N 15/86* | (2006.01) |
| *A61K 39/00* | (2006.01) |
| *C07K 16/16* | (2006.01) |
| *A61K 48/00* | (2006.01) |
| *C07K 14/005* | (2006.01) |
| *A61K 39/395* | (2006.01) |
| *A61K 39/12* | (2006.01) |
| *A61K 35/76* | (2015.01) |
| *A61K 9/00* | (2006.01) |
| *C12N 7/00* | (2006.01) |
| *C12N 15/79* | (2006.01) |
| *C12N 15/864* | (2006.01) |

(52) U.S. Cl.
CPC .......... *C12N 15/86* (2013.01); *A61K 39/0013* (2013.01); *C07K 16/16* (2013.01); *C12N 2710/10042* (2013.01); *C12N 2750/14143* (2013.01)

(58) Field of Classification Search
CPC .......... A61K 2039/505; A61K 48/0083; A61K 39/395; A61K 39/12; A61K 35/76; A61K 39/00; A61K 9/0019; A61K 2039/5256; C12N 7/00; C12N 15/86; C12N 2750/14143; C12N 15/79; C12N 15/8645; C12N 2750/14142; C12N 2750/14141; C12N 2750/14152; C12N 2750/14334; C07K 14/005; C07K 14/015; C07K 16/16
See application file for complete search history.

(56) References Cited

U.S. PATENT DOCUMENTS

| | | | |
|---|---|---|---|
| 2003/0138772 A1* | 7/2003 | Gao | C07K 14/005 435/5 |
| 2005/0013809 A1* | 1/2005 | Owens | C07K 16/44 424/130.1 |
| 2006/0034805 A1* | 2/2006 | Fang | C07K 16/00 424/93.2 |
| 2011/0086063 A1* | 4/2011 | Crystal | A61K 39/0013 424/199.1 |
| 2011/0123541 A1* | 5/2011 | Bachmann | C07K 16/00 424/142.1 |
| 2012/0232133 A1* | 9/2012 | Balazs | C07K 16/1045 514/44 R |
| 2013/0011432 A1* | 1/2013 | Crystal et al. | 424/196.11 |

FOREIGN PATENT DOCUMENTS

| | | | | |
|---|---|---|---|---|
| WO | WO 02058635 A2 * | 8/2002 | | C07D 207/06 |
| WO | WO 2011/116189 A1 | 9/2011 | | |
| WO | WO-2011116189 A1 * | 9/2011 | | A61K 39/0013 |
| WO | WO 2011127989 A1 * | 10/2011 | | A61K 39/0013 |

OTHER PUBLICATIONS

Moreno AY, Janda KD. Immunopharmacotherapy: vaccination strategies as a treatment for drug abuse and dependence. Pharmacol Biochem Behav. 2009.*
Fang J, Yi S, Simmons A, Tu GH, Nguyen M, Harding TC, VanRoey M, Jooss K. An antibody delivery system for regulated expression of therapeutic levels of monoclonal antibodies in vivo. Mol Ther. Jun. 2007;15(6):1153-9. Epub Mar. 20, 2007.*
Rapti K, Louis-Jeune V, Kohlbrenner E, Ishikawa K, Ladage D, Zolotukhin S, Hajjar RJ, Weber T. Neutralizing antibodies against AAV serotypes 1, 2, 6, and 9 in sera of commonly used animal models. Mol Ther. Jan. 2012;20(1):73-83. Epub Sep. 13, 2011.*
Alberg et al., Epidemiology of Lung Cancer: Looking to the Future, *Journal of Clinical Oncology*, 23(14): 3175-3185 (2005).
Benowitz et al., Daily intake of nicotine during cigarette smoking, *Clin. Pharmacol. Ther.*, 35: 499-504 (1984).

(Continued)

*Primary Examiner* — Rachel B Gill
(74) *Attorney, Agent, or Firm* — Leydig, Voit & Mayer, Ltd.

(57) ABSTRACT

The invention is directed to an adeno-associated virus (AAV) vector which comprises a nucleic acid sequence encoding an antibody or antigen binding fragment that binds to nicotine or a nicotine analog. The invention also is directed to a composition comprising the AAV vector and methods of using the AAV vector to induce an immune response against nicotine in a mammal.

12 Claims, 8 Drawing Sheets

Figure 1A:
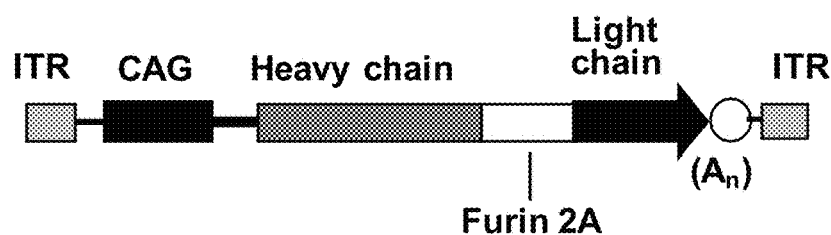

Specification includes a Sequence Listing.

(56) References Cited

OTHER PUBLICATIONS

Benowitz, N.L., Pharmacology of nicotine: addiction, smoking-induced disease, and therapeutics, *Annu. Rev. Pharmacol. Toxicol.*, 49: 57-71 (2009).
Blanco-Cedres et al., Relation of cigarette smoking to 25-year mortality in middle-aged men with low baseline serum cholesterol: the Chicago Heart Association Detection Project in Industry, *Am. J. Epidemiol.*, 155: 354-360 (2002).
Butz et al., Long-term telemetric measurement of cardiovascular parameters in awake mice: a physiological genomics tool, *Physiol Genomics*, 5: 89-97 (2001).
Carrera et al., Investigations using immunization to attenuate the psychoactive effects of nicotine, *Bioorg. Med. Chem.*, 12: 563-570 (2004).
Carter, Adeno-Associated Virus Vectors in Clinical Trials, *Human Gene Therapy*, 16: 541-550 (2005).
Castro et al., Nicotine Antibody Production: Comparison of Two Nicotine Conjugates in Different Animal Species, *Biochemical and Biophysical Research Communications*, 67(2): 583-589 (1975).
Cearley et al., Transduction Characteristics of Adeno-associated Virus Vectors Expressing Cap Serotypes 7, 8, 9, and Rh10 in the Mouse Brain, *Molecular Therapy*, 13(3): 528-537 (2006).
Center for Disease Control and Prevention, Department of Health and Human Services, *Morbidity and Mortality Weekly Report, Malaria Surveillance—United States, 2008*, vol. 59, No. SS-7 (Jun. 25, 2010).
Cerny et al., "Preclinical Development of a Vaccine 'Against Smoking'", *Onkologie*, 25: 406-411 (2002).
Chiorini et al., Cloning and Characterization of Adeno-Associated Virus Type 5 *Journal of Virology*, 73(2): 1309-1319 (1999).
Chiorini et al., Cloning of Adeno-Associated Virus Type 4 (AAV4) and Generation of Recombinant AAV4 Particles *Journal of Virology*, 71(9): 6823-33 (1997).
Church et al., Free-Radical Chemistry of Cigarette Smoke and Its Toxicological Implications, *Environmental Health Perspectives*, 64: 111-126 (1985).
Daly et al., Neonatal gene transfer leads to widespread correction of pathology in a murine model of lysosomal storage disease, *Proc. Natl. Acad. Sci. U.S.A.*, 96: 2296-2300 (1999).
Damaj et al., Effects of hydroxymetabolites of bupropion on nicotine dependence behavior in mice. *Journal of Pharmacology and Experimental Therapeutics*, 334(3):1087-1095 (2010).
De Villiers et al., Active Immunization against Nicotine Suppresses Nicotine-Induced Dopamine Release in the Rat Nucleus accumbens Shell, *Respiration*, 69: 247-253 (2002).
Fang et al., Stable antibody expression at therapeutic levels using the 2A peptide, *Nature. Biotechnology*, 23(5): 584-590 (2005).
Fernandez et al., Acute ventilatory and circulatory reactions evoked by nicotine: are they excitatory or depressant?, *Respiratory Physiology & Neurobiology*, 133: 173-182 (2002).
Fiore et al., Treating Tobacco Use and Dependence: 2008 Update, *U.S. Dept. of Health and Human Services*, 1-276 (2008).
Fowler et al., Subtypes of nicotinic acetylcholine receptors in nicotine reward, dependence, and withdrawal: evidence from genetically modified mice, *Behav. Pharmacol.* 19(5-6), 461-484 (2008).
George et al., Individual differences in prefrontal cortex function and the transition from drug use to drug dependence, *Neurosci. Biobehav. Rev.* 35(2): 232-247 (2010).
Hatsukami et al., Immunogenicity and smoking-cessation outcomes for a novel nicotine immunotherapeutic, *Clin.Pharmacol. Ther.*, 89(3): 392-399 (2011).
Hicks et al.; AAV-Directed Persistent Expression of a Gene Encoding Anti-Nicotine Antibody for Smoking Cessation, *Sci Transl Med* 4, 140ra87 (2012).
Hieda et al., Vaccination against nicotine during continued nicotine administration in rats: immunogenicity of the vaccine and ejects on nicotine distribution to brain, *International Journal Immunopharmacology*, 22: 809-819 (2000).
Hieda et al., Active Immunization Alters the Plasma Nicotine Concentration in Rats, *Journal of Pharmacology and Experimental Therapeutics*, 283(3): 1076-1081 (1997).
Hylkema et al., Tobacco use in relation to COPD and asthma, *Eur. Respir. J.*, 29: 438-445 (2007).
Isomura et al., An Immunotherapeutic Program for the Treatment of Nicotine Addiction: Hapten Design and Synthesis, *J. Org. Chem.*, 66: 4115-4121 (2001).
Langone et al., Nicotine and Its Metabolites. Radioimmunoassays for Nicotine and Cotinine, *Biochemistry*, 12(24): 5025-5030 (1973).
Langone et al., Radioimmunoassay of Nicotine, Cotinine, and y-(3-Pyridyl)-y-oxo-N-methylbutyramide, *Methods in Enzymology*, 84: 628-640 (1982).
Le Houezec, Role of nicotine pharmacokinetics in nicotine addiction and nicotine replacement therapy: a review, *Int J. Tuberc. Lung Dis.*, 7(9): 811-819 (2003).
Lesage et al., Current Status of Immunologic Approaches to Treating Tobacco Dependence: Vaccines and Nicotine-specific Antibodies, *The AAPS. Journal*, 8(1): E65-E75 (2006).
Lindblom et al., Active Immunization against Nicotine Prevents Reinstatement of Nicotine-Seeking Behavior in Rats, *Respiration*, 69: 254-260 (2002).
Mao et al., AAV Delivery of Wild-Type Rhodopsin Preserves Retinal Function in a Mouse Model of Autosomal Dominant Retinitis Pigmentosa, *Human Gene Therapy*, 22: 567-575 (2011).
Mao et al., Persistent Suppression of Ocular Neovascularization with Intravitreal Administration of AAVrh.10 Coding for Bevacizumab, *Human Gene Therapy*, 22: 1525-1535 (2011).
Maskos, et al., Nicotine reinforcement and cognition restored by targeted expression of nicotinic receptors *Nature*, 436: 103-107 (2005).
Maurer et al., A therapeutic vaccine for nicotine dependence: preclinical efficacy, and Phase I safety and immunogenicity, *European Journal of Immunology.*, 35: 2031-2040 (2005).
Maurer et al., Vaccination against nicotine: an emerging therapy for tobacco dependence, *Expert. Opin. Investig. Drugs*, 16: 1775-1783 (2007).
Meijler et al., A New Strategy for Improved Nicotine Vaccines Using Conformationally Constrained Haptens, *J. Am. Chem. Soc.*, 125: 7164-7165 (2003).
Moreno et al., A Critical Evaluation of a Nicotine Vaccine within a Self-Administration Behavioral Model, *Molecular Pharmaceutics*, 7(2): 431-441 (2010).
Moreno et al., Immunopharmacotherapy: Vaccination Strategies as a Treatment for Drug Abuse and Dependence, *Pharmacol. Biochem. Behav.*, 92(2): 199-205 (2009).
Müller,R., Determination of Affinity and Specificity of Anti-Hapten Antibodies by Competitive Radioimmunoassay, *Methods in Enzymology*, 92: 589-601 (1983).
Nadeau et al., Effects of nicotine on heart rate studied by direct perfusion of sinus code, *Am. J. Physiol*, 212: 911-916 (1967).
National Cancer Institute, in Smoking and Tobacco Control. Cigars: Health Effects and Trends, *NCI Tobacco Control Monograph*, 9: 61 (2011).
Niwa et al., Efficient selection for high-expression transfectants with a novel eukaryotic vector, *Gene*, 108: 193-199 (1991).
Noguchi et al., Conjugate of Nicotine and Cotinine to Bovine Serum Albumin, *Biochemical and Biophysical Research Communications*, 83(1): 83-86 (1978).
Pentel et al., A Nicotine Conjugate Vaccine Reduces Nicotine Distribution to Brain and Attenuates Its Behavioral and Cardiovascular Effects in Rats, *Pharmacology Biochemistry and Behavior*, 65(1): 191-198 (2000).
Pollack, A, "Antismoking Vaccine Fails in Late Trial," *The New York Times* (Jul. 18, 2011).
Polosa et al., Treatment of nicotine addiction: present therapeutic options and pipeline developments, *Trends Pharmacol. Sci.*, 32(5): 281-289 (2011).
Pryor et al., Oxidants in Cigarette Smoke. Radicals, Hydrogen Peroxide, Peroxynitrate, and Peroxynitrite, *Ann. N. Y. Acad. Sci.*, 686: 12-27 (1993).
Robertson et al., Smoking and mechanisms of cardiovascular control, *Am. Heart J.*, 115: 258-263 (1988).

(56) References Cited

OTHER PUBLICATIONS

Rose et al., Arterial nicotine kinetics during cigarette smoking and intravenous nicotine administration: implications for addiction, *Drug Alcohol Depend.*, 56: 99-107 (1999).
Rutledge et al., *Infectious Clones and Vectors Derived from Adeno-Associated Virus (AAV) Serotypes Other Than AAV Type 2, Journal of Virology*, 72(1): 309-319 (1998).
Sebelius, K., How Tobacco Smoke Causes Disease:the Biology and Behavioral Basis for Smoking-Attributable Disease: a Report of the Surgeon General, *U.S. Dept. of Health and Human Services* (2010).
Singh et al., Risk of serious adverse cardiovascular events associated with varenicline: a systematic review and meta-analysis, *CMAJ*, 183(12): 1359-1366 (2011).
Sondhi et al., Enhanced Survival of the LINCL Mouse Following CLN2 Gene Transfer Using the rh.10 Rhesus Macaque-derived Adeno-associated Virus Vector, *Molecular Therapy*, 15(3): 481-491 (2007).
Srivastava et al., Nucleotide Sequence and Organization of the Adeno-Associated Virus 2 Genome *Journal of Virology*, 45(2): 555-64 (1983).
Stead et al., Nicotine replacement therapy for smoking cessation (Review), The *Cochrane Collaboration*, Article No. CD000146 (2008).
Tammimaki et al., Recent advances in gene manipulation and nicotinic acetylcholine receptor biology, *Biochem. Pharmacol.*, 82(8): 808-819 (2011).
Tuncok et al., Inhibition of Nicotine-Induced Seizures in Rats by Combining Vaccination Against Nicotine With Chronic Nicotine Infusion, *Experimental and Clinical Psychopharmacology*, 9(2): 228-234 (2001).
Watanabe et al., AAVrh.10-mediated genetic delivery of bevacizumab to the pleura to provide local anti-VEGF to suppress growth of metastatic lung tumors, *Gene Therapy*, 17(8): 1042-1051 (2010).
Wu et al., Adeno-associated Virus Serotypes: Vector Toolkit for Human Gene Therapy, *Molecular Therapy*, 14(3): 316-327 (2006).
Wu et al., Mutational Analysis of the Adeno-Associated Virus Type 2 (AAV2) Capsid Gene and Construction of AAV2 Vectors with Altered Tropism *Journal of Virology*, 74(18): 8635-47 (2000).
Xiao et al., Production of High-Titer Recombinant Adeno-Associated Virus Vectors in the Absence of Helper Adenovirus, *Journal of Virology*, 72(3), 2224-2232 (1998).
GenBank Accession Record No. U89790.1, submitted on Aug. 21, 1997.
GenBank Accession Record No. J01901.1, submitted on Apr. 27, 1993.
GenBank Accession Record No. AF043303.1, submitted on May 20, 2010.
GenBank Accession Record No. AF085716.1, submitted on Feb. 9, 1999.
De et al., Vaccines Based on Disrupted Ad5 Against Small Molecule Drugs Are Efficacious in the Presence of Preexisting Ad5 Immunity, *Molecular Therapy*, 20(Suppl. 1): S156-S157 (2012).
Keyler et al., Monoclonal nicotine-specific antibodies reduce nicotine distribution to brain in rats: dose- and affinity-response relationships, *Drug Metabolism and Disposition*, 33(7): 1056-1061 (2005).
Lv et al., Adeno-associated virus-mediated anti-DR5 chimeric antibody expression suppresses human tumor growth in nude mice, *Cancer Letters*, 302(2):119-127 (2011).
Rosenberg et al., AAVrh.10-Mediated Expression of an Anti-Cocaine Antibody Mediates Persistent Passive Immunization That Suppresses Cocaine-Induced Behavior, *Human Gene Therapy*, 23(5): 451-459 (2012).
European Patent Office, International Search Report in Application No. PCT/US2013/027619 (dated May 2, 2013).

\* cited by examiner

AAVantiNic (AAVrh.10antiNic.Mab)

Coomassie blue

Western

Persistence

Dose-dependence

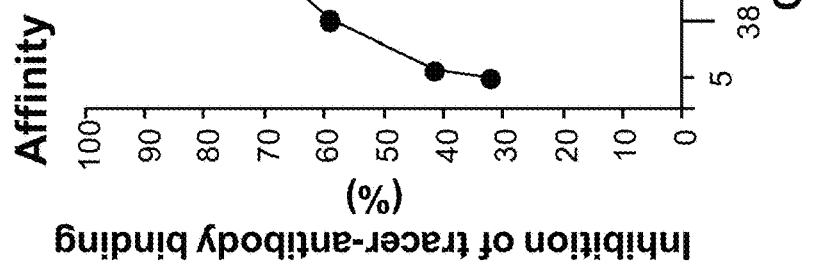
Fig. 2D Affinity
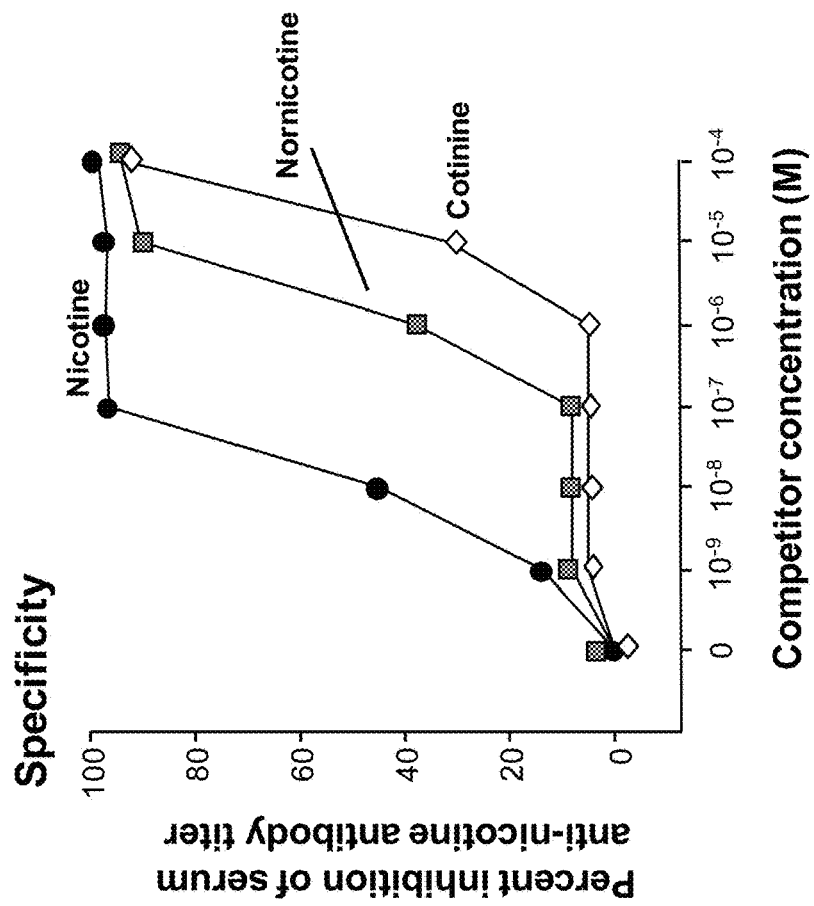
Fig. 2C Specificity

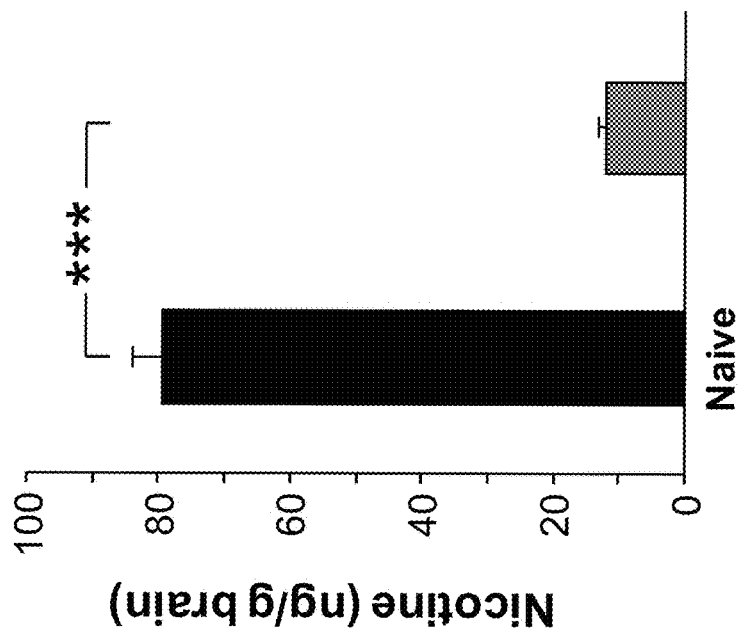
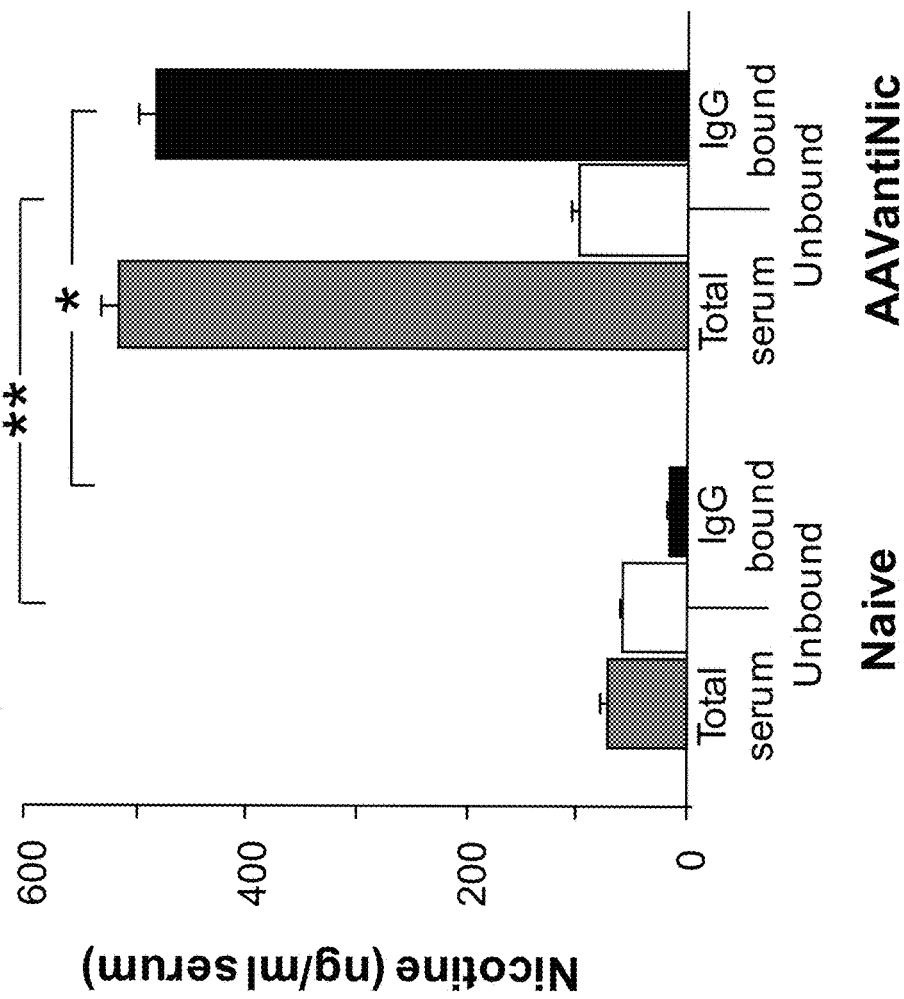

Mean arterial blood pressure

Heart rate

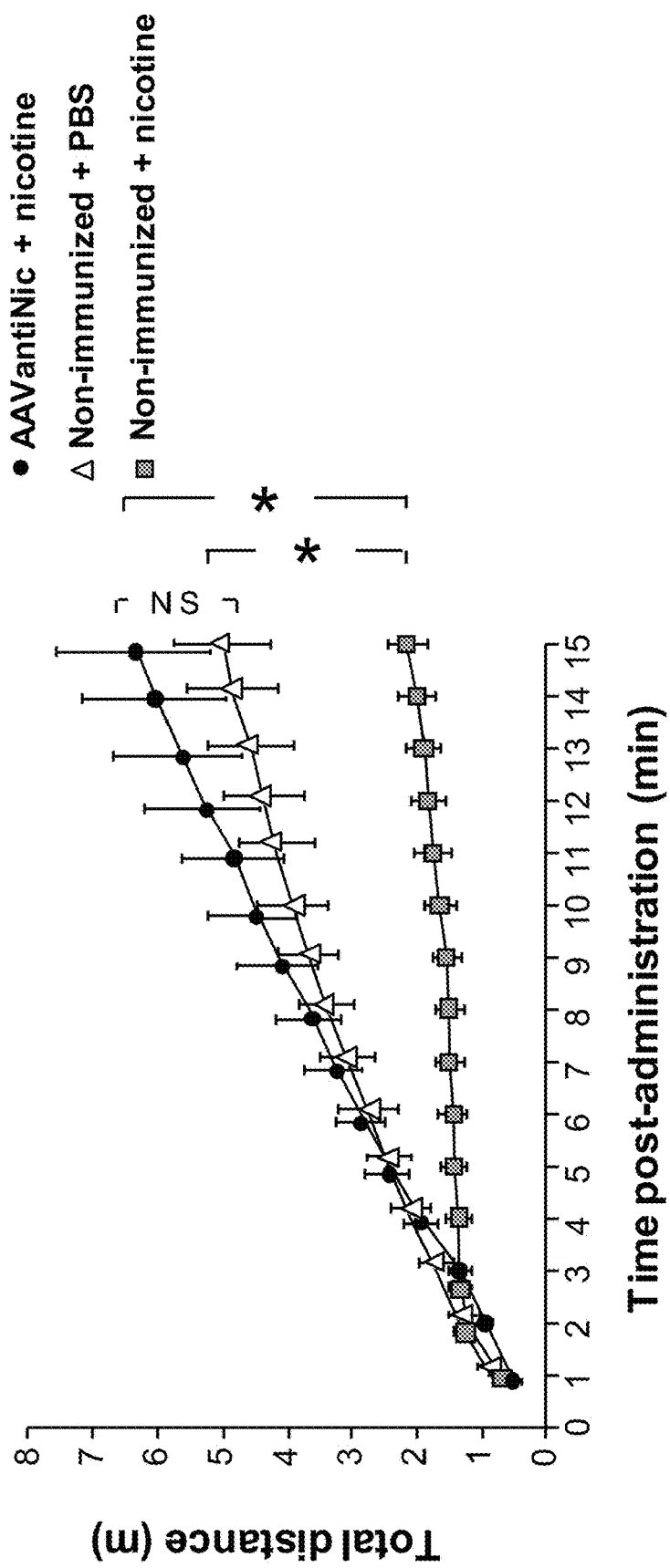

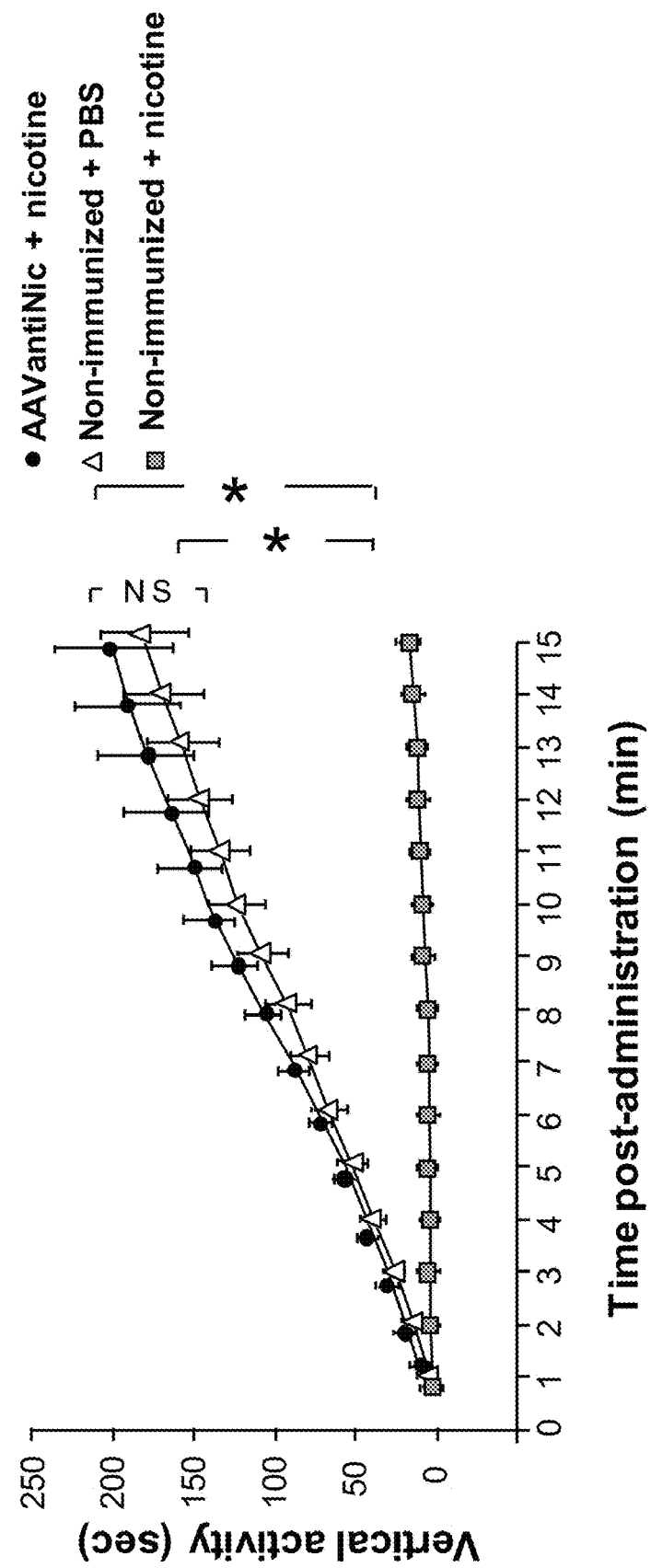

AAV-DIRECTED PERSISTENT EXPRESSION OF AN ANTI-NICOTINE ANTIBODY GENE FOR SMOKING CESSATION

CROSS-REFERENCE TO RELATED APPLICATIONS

This patent application claims the benefit of U.S. Provisional Patent Application No. 61/604,203 filed Feb. 28, 2012, which is incorporated by reference in its entirety herein.

STATEMENT REGARDING FEDERALLY SPONSORED RESEARCH AND DEVELOPMENT

This invention was made with Government support under Grant Number DA025305 awarded by the National Institutes of Health. The Government has certain tights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 9,501 Byte ASCII (Text) file named "718498_ST25.TXT," created on Aug. 26, 2014.

BACKGROUND OF THE INVENTION

The most widely used addictive drug in the world is tobacco, of which the principal addictive component is nicotine. Approximately 20.6% of adults in the U.S. smoke cigarettes, and cigarette smoking accounts for one of every five deaths in the USA (Center for Disease Control and Prevention, Morbidity and Mortality Weekly Report. *Centers for Disease Control* 10 A.D. September; vol. 59 (2012)). In the lung, cigarette smoke causes chronic obstructive pulmonary disease (COPD) and lung cancer, and smoking is associated with an increased risk of cardiovascular disease and a variety of other neoplasms (see, e.g., Alberg et al., *J. Clin. Oncol.*, 23: 3175-3185 (2005); Blanco-Cedres et al., *Am. J. Epidemiol.*, 155: 354-360 (2002); Hylkema et al., *Eur. Respir. J.*, 29: 438-445 (2007); and Sebelius K, *How Tobacco Smoke Causes Disease: the Biology and Behavioral Basis for Smoking-Attributable Disease: a Report of the Surgeon General*, U.S. Dept. of Health and Human Services (2010)). Smoking-related health care and loss of productivity cost in excess of $193 billion annually in the U.S. (Sebelius, supra).

Although each puff of cigarette smoke contains more than 4000 chemicals, the addictive properties of cigarette smoking are due to nicotine, a 162 Da alkaloid that represents 0.6-3.0% of dry weight of tobacco (see, e.g., National Cancer Institute (NCI) Tobacco Control Monograph, 9: 61 (2011); Church et al., *Environ. Health Perspect.*, 64: 111-126 (1985); and Pryor et al., *Ann. N.Y. Acad. Sci.*, 686: 12-27 (1993)). Most nicotine is pyrolized at the cigarette tip, but each cigarette typically delivers 1.0 to 1.5 mg nicotine that passes across the alveoli into the blood stream, taking about 10 to 19 seconds to reach the brain (see, e.g., Rose et al., *Drug Alcohol Depend.*, 56: 99-107 (1999); Le Houezec, J., *Int J. Tuberc. Lung Dis.*, 7: 811-819 (2003); and Benowitz et al., *Clin. Pharmacol. Ther.*, 35: 499-504 (1984)). In the brain, nicotine binds to the nicotinic acetylcholine receptor, triggering L-tyrosine to be converted to dopamine, with resulting pleasure, reduced stress, alterations in blood pressure and heart rate, heightened alertness and increased ability to process information (see, e.g., Tammimaki et al., *Biochem. Pharmacol.*, 82(8): 808-19 (2011); Maskos, et al., *Nature*, 436: 103-107 (2005); and Benowitz, N. L., *Annu. Rev. Pharmacol. Toxicol.*, 49: 57-71 (2009)).

Despite the devastating effects of nicotine addiction, the combined current strategies with drugs and counseling to help smokers quit are mostly ineffective, with a 70 to 80% recidivism rate within 6 months (see, e.g., Fiore, M. C., et al., *Treating Tobacco Use and Dependence:* 2008 Update, U.S. Dept. of Health and Human Services). One approach to treating nicotine addiction has been to develop an anti-nicotine vaccine. Anti-nicotine vaccines attempt to generate a host immune response to evoke humoral immunity against nicotine. The challenge of this approach is that nicotine is a small molecule not seen by the immune system, and thus nicotine (or a nicotine analog) must be coupled to a larger molecule to induce an anti-nicotine immune response (Lesage et al., *AAPS. J.*, 8: E65-E75 (2006); Moreno et al., *Pharmacol. Biochem. Behav.*, 92: 199-205 (2009); and Maurer et al., *Eur. J. Immunol.*, 35: 2031-2040 (2005)). For example, AM1, a trans-3'-(hydroxymethyl) nicotine-derived nicotine hapten with a linker containing an ether moiety and a free carboxyl group for conjugation, has been attached to carriers such as tetanus toxin to create an anti-nicotine vaccine. In a rodent self-administration model, this vaccine shifted preference for nicotine self-administration (see Moreno et al., *Mol. Pharm.*, 7: 431-441 (2010)). Three active immunotherapy vaccines have been tested in clinical trials, including TA-NIC (a nicotine analog linked to cholera toxin B, Xenova), NicVAX (a nicotine analog linked to *Pseudomonas aeruginosa* exoprotein A, Nabi Pharmaceuticals), and NicQb (a nicotine analog linked to particles of the bacteriophage Qβ, Cytos Biotechnology) (see Polosa et al., *Trends Pharmacol. Sci.*, 32: 281-289 (2011); and Hatsukami et al., *Clin. Pharmacol. Ther.*, 89: 392-399 (2011)). These vaccines are well tolerated, and the individuals with the highest levels of antibodies were more likely to abstain from smoking (see Polosa et al., supra). However, all trials showed large variation among trial participants in the amount of antibody generated, and only a relatively small percentage of the participants have abstained from smoking (see Polosa et al., supra, Hatsukami et al., supra; Maurer et al., *Expert. Opin. Investig. Drugs*, 16: 1775-1783 (2007); and Pollack, A, "Antismoking Vaccine Fails in Late Trial," *The New York Times* (Jul. 18, 2011)).

Thus, there is a need for alternative compositions and methods to prevent or treat nicotine addiction. This invention provides such compositions and methods. This and other advantages of the invention will become apparent from the detailed description provided herein.

BRIEF SUMMARY OF THE INVENTION

The invention provides an adeno-associated virus (AAV) vector comprising a nucleic acid sequence which encodes an antibody that binds to nicotine or a nicotine analog, or an antigen-binding fragment thereof. The invention also provides a composition comprising the AAV vector and methods of using the AAV vector to induce an immune response against nicotine in a mammal.

BRIEF DESCRIPTION OF THE SEVERAL VIEWS OF THE DRAWING(S)

Figure 1B:
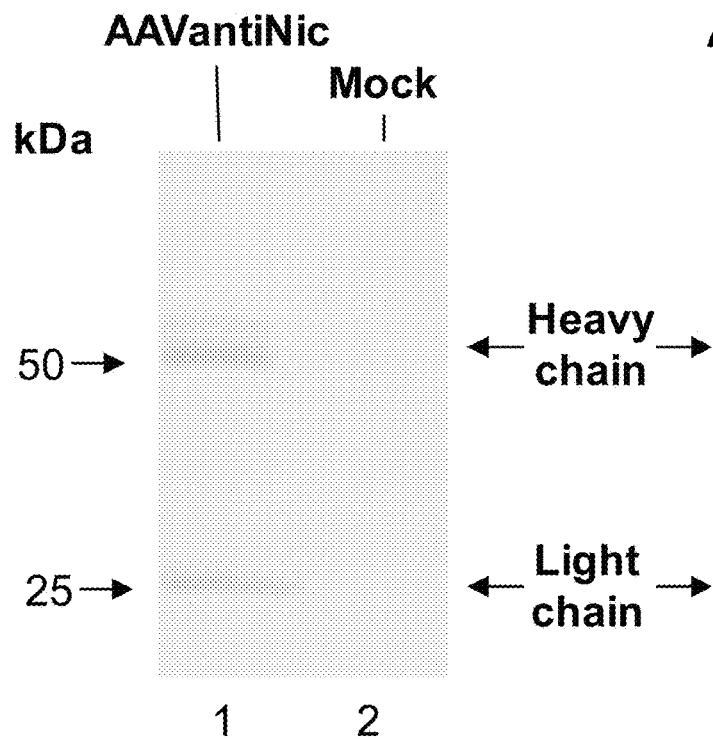
Figure 1C:
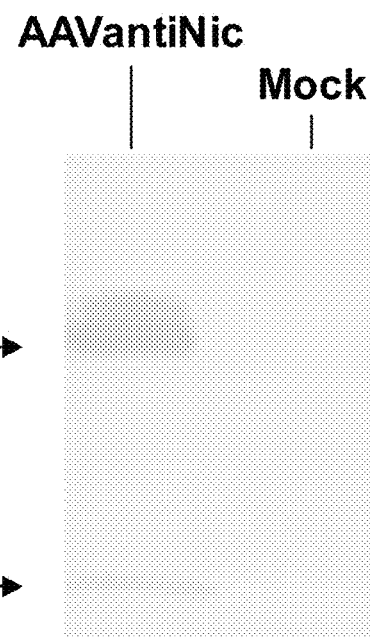

FIG. 1A is a schematic of the AAVantiNic vector, which depicts the CMV enhancer/chicken β-actin promoter (CAG promoter), nucleic acid sequences encoding the heavy and light chain polypeptides of the anti-nicotine monoclonal antibody NIC9D9, furin-2a polypeptide cleavage site, and poly A signal. FIGS. 1B and 1C are images which depict expression of the anti-nicotine antibody encoded by the AAVantiNic vector in HEK 293 cells under reducing conditions, as analyzed by coomassie blue staining (FIG. 1B) and Western blot using a sheep anti-mouse IgG antibody (FIG. 1C).

Figure 2B:
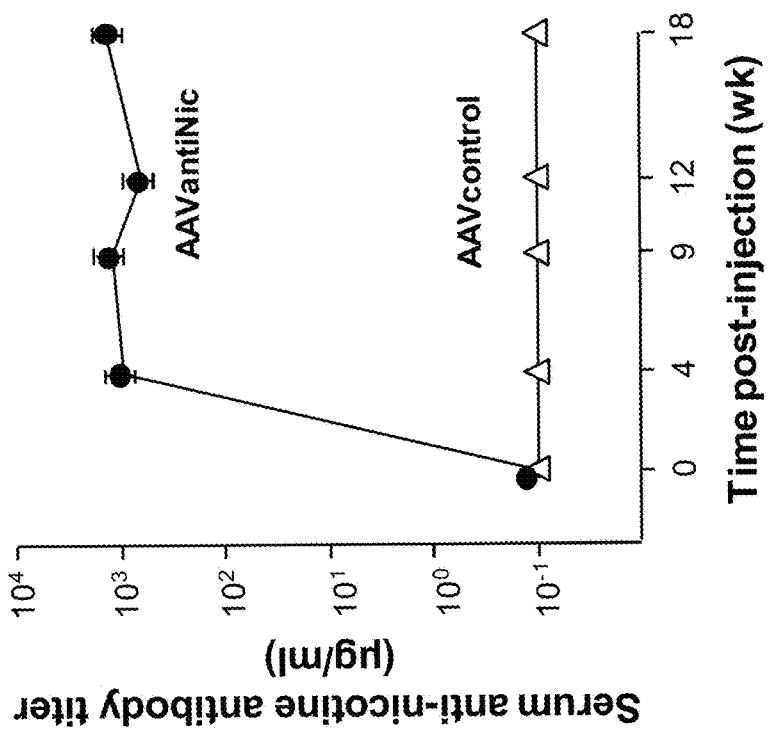
Figure 2A:
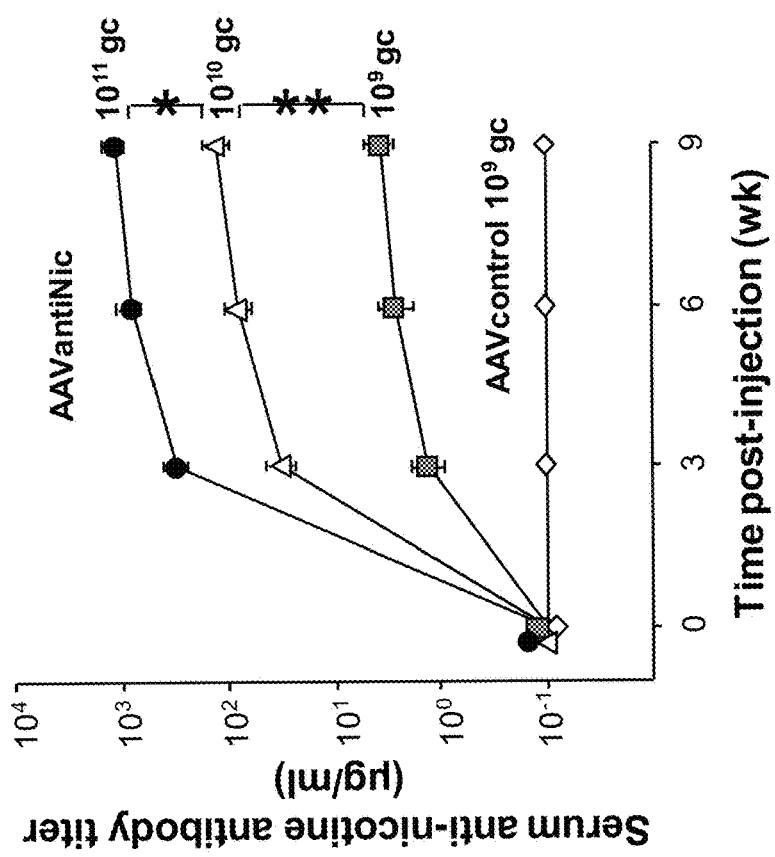

FIGS. 2A-2D are graphs which depict experimental data illustrating AAVantiNic-directed expression of an anti-nicotine antibody in mice, as described in Example 2. FIG. 2A depicts anti-nicotine IgG antibody titers as a function of increasing dosage of AAVantiNic. Antibody titers were assessed by ELISA against bovine-serum-albumin (BSA) conjugated-nicotine hapten AM1 ($*p<0.005$, $**p<0.0003$). FIG. 2B depicts the persistence of expression of the anti-nicotine antibody following administration of AAVantiNic over 18 weeks. For FIGS. 2A and 2B, antibody titers were determined compared to a NIC9D9 antibody standard. FIG. 2C depicts the specificity of the anti-nicotine antibody generated by AAVantiNic in vitro Inhibition of binding of immune sera to BSA-AM1 by ELISA was performed in the presence of increasing concentrations of nicotine, nornicotine, or cotinine FIG. 2D depicts the serum anti-nicotine antibody affinity (Kd) generated by AAVantiNic. Serum used in FIG. 2C was used to determine the Kd by inhibition of tracer ($3^H$-nicotine) binding via a cold competitor radioimmunoassay.

FIGS. 3A and 3B are graphs which depict experimental data illustrating the levels of nicotine in serum (FIG. 3A) and brain (FIG. 3B) of C57Bl/6 mice challenged with nicotine, as described in Example 3. Shown are nicotine levels in the serum (ng/ml serum) (FIG. 3A) and brain (ng/g brain) (FIG. 3B) of non-immunized and AAVantiNic-immunized mice 15 weeks post-administration with AAVantiNic. Blood nicotine levels are depicted in FIG. 3A, and the data includes: total serum nicotine, unbound nicotine, and IgG bound nicotine ($*p<10^{-5}$, $p<0.005$). Brain nicotine levels are depicted in FIG. 3B, which shows data for non-immunized and AAVantiNic immunized mice ($*p<10^{-4}$). Comparisons between groups were conducted by a two-tailed unpaired t-test.

Figure 4A:
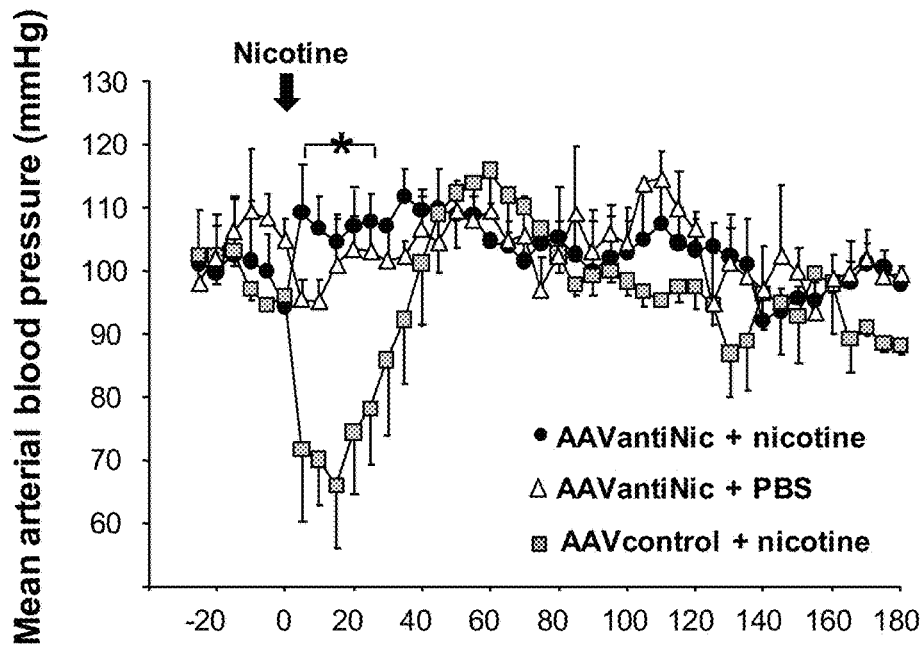
Figure 4B:
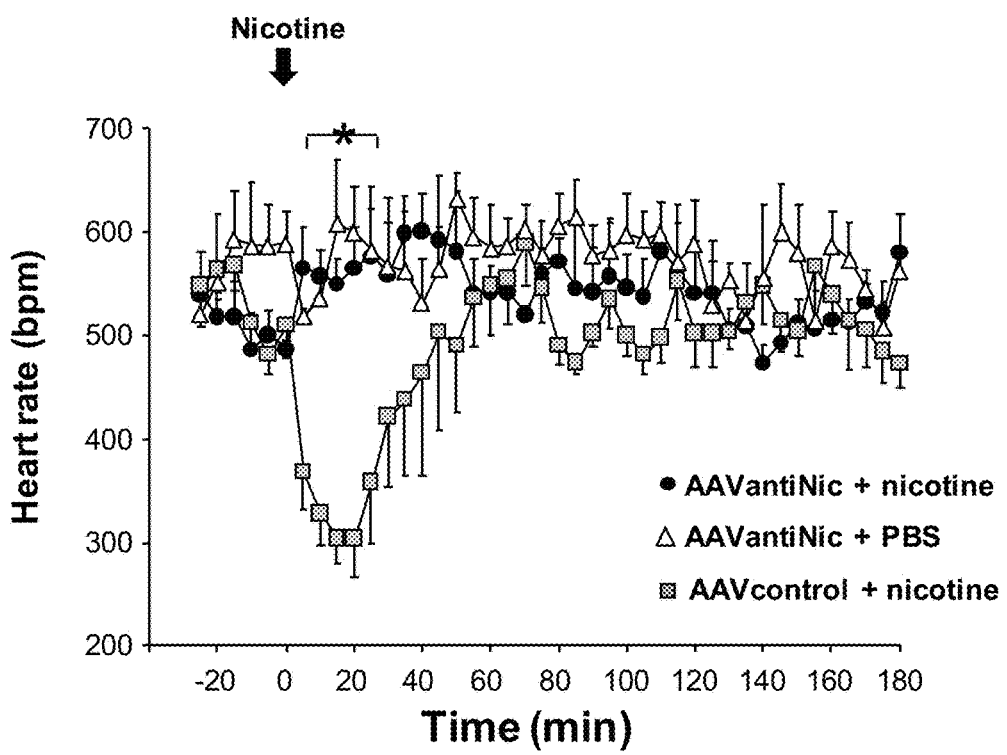

FIGS. 4A and 4B are graphs which depict experimental data illustrating the prevention of nicotine-induced cardiovascular effects by AAVantiNic, as described in Example 4. FIG. 4A depicts base-line mean arterial blood pressure (MAP), and FIG. 4B depicts heart rate (HR) of AAVantiNic-immunized or AAVcontrol treated-mice. AAVantiNic abolished nicotine-induced MAP depressor and HR bradycardic responses during the first 25 minutes ($* p<10^{-3}$) following injection. Comparisons between groups were conducted by two-way repeated measures ANOVA. For both FIGS. 4A and 4B, data is shown for AAVantiNic-immunized mice administered nicotine (●), AAVantiNic-immunized mice administered PBS (A), and control mice administered nicotine (▩).

Figure 5A:
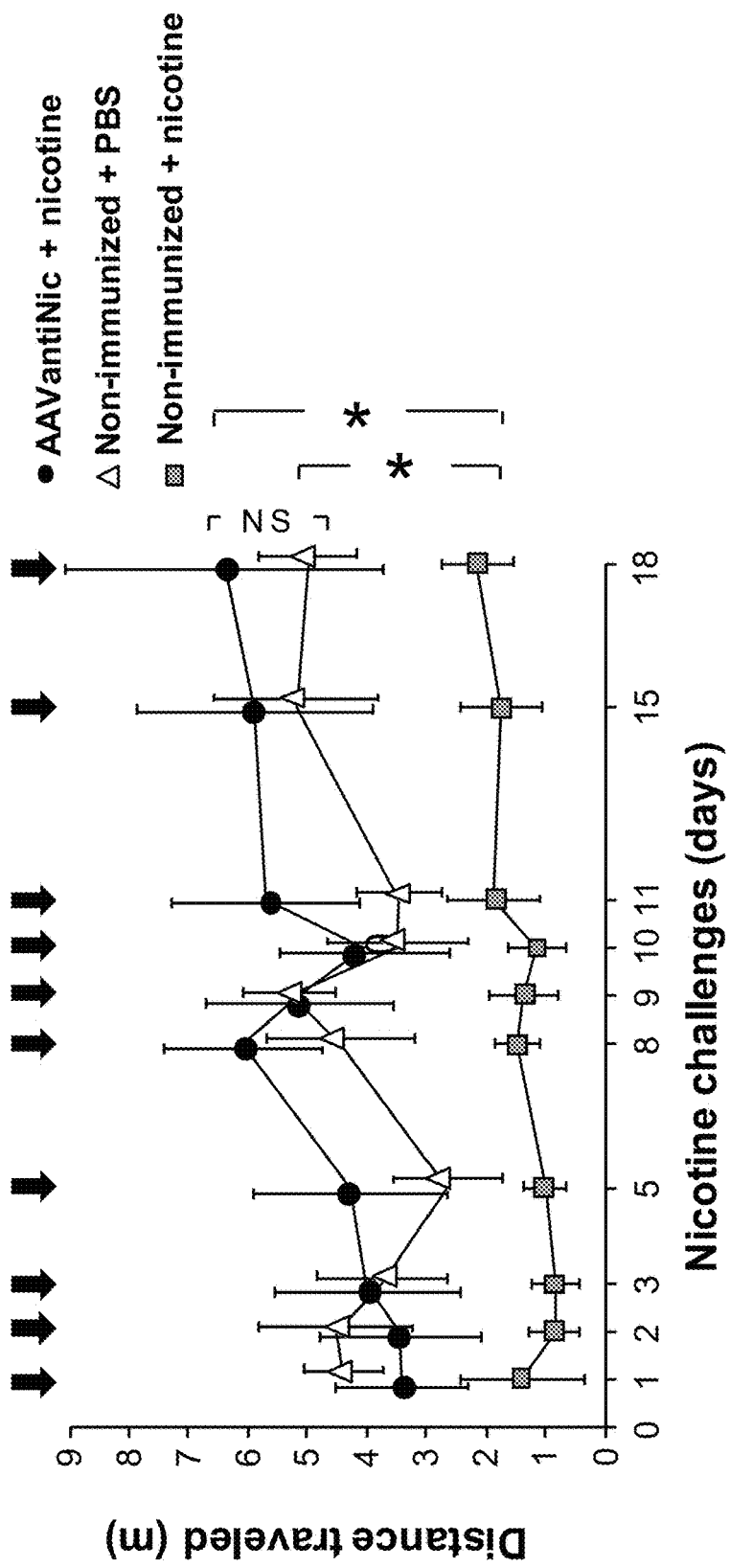

FIGS. 5A-5C are graphs which depict experimental data illustrating AAVantiNic-mediated prevention of nicotine-induced hypolocomotor activity, as described in Example 5. FIG. 5A shows the total distance traveled of non-immunized mice compared to AAVantiNic-immunized mice over time with frequent challenge with nicotine or PBS as indicated by the arrows (AAVantiNic-immunized mice+nicotine (●); non-immunized mice+nicotine (▩); and non-immunized mice+PBS (Δ) (NS p=0.15, $*p<10^{-5}$). FIG. 5B shows examples of cumulative distance traveled assessed as a function of time post-administration of PBS or nicotine (7 week post-single administration of the AAVantiNic (NS p>0.7, $*p<10^{-3}$). FIG. 5C shows cumulative vertical activity assessed as a function of time post-administration of PBS or nicotine in the same mice as in FIG. 5B (NS p=0.91, $*p<10^{-4}$).

DETAILED DESCRIPTION OF THE INVENTION

The invention is predicated, at least in part, on the ability of adeno-associated virus (AAV) vectors to be safely administered to humans and to provide persistent expression of a therapeutic transgene. The invention provides an adeno-associated virus (AAV) vector which comprises, consists essentially of, or consists of a nucleic acid sequence encoding an antibody that binds to nicotine or a nicotine analog, or an antigen-binding fragment thereof. When the inventive AAV vector consists essentially of a nucleic acid sequence encoding an antibody that binds to nicotine or a nicotine analog, or an antigen-binding fragment thereof, additional components can be included that do not materially affect the AAV vector (e.g., genetic elements such as poly(A) sequences or restriction enzyme sites that facilitate manipulation of the vector in vitro). When the AAV vector consists of a nucleic acid sequence encoding an antibody that binds to nicotine or a nicotine analog, or an antigen-binding fragment thereof, the AAV vector does not comprise any additional components (i.e., components that are not endogenous to AAV and are not required to effect expression of the nucleic acid sequence to thereby provide the antibody).

Adeno-associated virus is a member of the Parvoviridae family and comprises a linear, single-stranded DNA genome of less than about 5,000 nucleotides. AAV requires co-infection with a helper virus (i.e., an adenovirus or a herpes virus), or expression of helper genes, for efficient replication. AAV vectors used for administration of therapeutic nucleic acids typically have approximately 96% of the parental genome deleted, such that only the terminal repeats (ITRs), which contain recognition signals for DNA replication and packaging, remain. This eliminates immunologic or toxic side effects due to expression of viral genes. In addition, delivering specific AAV proteins to producing cells enables integration of the AAV vector comprising AAV ITRs into a specific region of the cellular genome, if desired (see, e.g., U.S. Pat. Nos. 6,342,390 and 6,821,511). Host cells comprising an integrated AAV genome show no change in cell growth or morphology (see, for example, U.S. Pat. No. 4,797,368).

The AAV ITRs flank the unique coding nucleotide sequences for the non-structural replication (Rep) proteins and the structural capsid (Cap) proteins (also known as virion proteins (VPs)). The terminal 145 nucleotides are self-complementary and are organized so that an energetically stable intramolecular duplex forming a T-shaped hairpin may be formed. These hairpin structures function as an origin for viral DNA replication by serving as primers for the cellular DNA polymerase complex. The Rep genes encode the Rep proteins Rep78, Rep68, Rep52, and Rep40. Rep78 and Rep68 are transcribed from the p5 promoter, and Rep 52 and Rep40 are transcribed from the p19 promoter. The Rep78 and Rep68 proteins are multifunctional DNA binding proteins that perform helicase and nickase functions during productive replication to allow for the resolution of AAV termini (see, e.g., Im et al., *Cell*, 61: 447-57 (1990)). These proteins also regulate transcription from endogenous AAV promoters and promoters within helper viruses (see, e.g., Pereira et al., *J. Virol.*, 71: 1079-1088 (1997)). The other Rep proteins modify the function of Rep78 and Rep68. The cap genes encode the capsid proteins VP1, VP2, and VP3. The cap genes are transcribed from the p40 promoter.

The inventive AAV vector can be generated using any AAV serotype known in the art. Several AAV serotypes and over 100 AAV variants have been isolated from adenovirus stocks or from human or nonhuman primate tissues (reviewed in, e.g., Wu et al., *Molecular Therapy*, 14(3): 316-327 (2006)). Generally, the AAV serotypes have genomic sequences of significant homology at the nucleic acid sequence and amino acid sequence levels, such that different serotypes have an identical set of genetic functions, produce virions which are essentially physically and functionally equivalent, and replicate and assemble by practically identical mechanisms. AAV serotypes 1-6 and 7-9 are defined as "true" serotypes, in that they do not efficiently cross-react with neutralizing sera specific for all other existing and characterized serotypes. In contrast, AAV serotypes 6, 10 (also referred to as Rh10), and 11 are considered "variant" serotypes as they do not adhere to the definition of a "true" serotype. AAV serotype 2 (AAV2) has been used extensively for gene therapy applications due to its lack of pathogenicity, wide range of infectivity, and ability to establish long-term transgene expression (see, e.g., Carter, B. J., *Hum. Gene Ther.*, 16: 541-550 (2005); and Wu et al., supra). Genome sequences of various AAV serotypes and comparisons thereof are disclosed in, for example, GenBank Accession numbers U89790, J01901, AF043303, and AF085716; Chiorini et al., *J. Virol.*, 71: 6823-33 (1997); Srivastava et al., *J. Virol.*, 45: 555-64 (1983); Chiorini et al., *J. Virol.*, 73: 1309-1319 (1999); Rutledge et al., *J. Virol.*, 72: 309-319 (1998); and Wu et al., *J. Virol.*, 74: 8635-47 (2000)).

AAV rep and ITR sequences are particularly conserved across most AAV serotypes. For example, the Rep78 proteins of AAV2, AAV3A, AAV3B, AAV4, and AAV6 are reportedly about 89-93% identical (see Bantel-Schaal et al., *J. Virol.*, 73(2): 939-947 (1999)). It has been reported that AAV serotypes 2, 3A, 3B, and 6 share about 82% total nucleotide sequence identity at the genome level (Bantel-Schaal et al., supra). Moreover, the rep sequences and ITRs of many AAV serotypes are known to efficiently cross-complement (i.e., functionally substitute) corresponding sequences from other serotypes during production of AAV particles in mammalian cells.

Generally, the cap proteins, which determine the cellular tropicity of the AAV particle, and related cap protein-encoding sequences, are significantly less conserved than Rep genes across different AAV serotypes. In view of the ability Rep and ITR sequences to cross-complement corresponding sequences of other serotypes, the AAV vector can comprise a mixture of serotypes and thereby be a "chimeric" or "pseudotyped" AAV vector. A chimeric AAV vector typically comprises AAV capsid proteins derived from two or more (e.g., 2, 3, 4, etc.) different AAV serotypes. In contrast, a pseudotyped AAV vector comprises one or more ITRs of one AAV serotype packaged into a capsid of another AAV serotype. Chimeric and pseudotyped AAV vectors are further described in, for example, U.S. Pat. No. 6,723,551; Flotte, *Mol. Ther.*, 13(1): 1-2 (2006); Gao et al., *J. Virol.*, 78: 6381-6388 (2004); Gao et al., *Proc. Natl. Acad. Sci. USA*, 99: 11854-11859 (2002); De et al., *Mol. Ther.*, 13: 67-76 (2006); and Gao et al., *Mol. Ther.*, 13: 77-87 (2006).

In one embodiment, the AAV vector is generated using an AAV that infects humans (e.g., AAV2). Alternatively, the AAV vector is generated using an AAV that infects non-human primates, such as, for example, the great apes (e.g., chimpanzees), Old World monkeys (e.g., macaques), and New World monkeys (e.g., marmosets). Preferably, the AAV vector is generated using an AAV that infects a non-human primate pseudotyped with an AAV that infects humans. Examples of such pseudotyped AAV vectors are disclosed in, e.g., Cearley et al., *Molecular Therapy*, 13: 528-537 (2006). In one embodiment, an AAV vector can be generated which comprises a capsid protein from an AAV that infects rhesus macaques pseudotyped with AAV2 inverted terminal repeats (ITRs). In a particularly preferred embodiment, the inventive AAV vector comprises a capsid protein from AAV10 (also referred to as "AAVrh.10"), which infects rhesus macaques pseudotyped with AAV2 ITRs (see, e.g., Watanabe et al., *Gene Ther.*, 17(8): 1042-1051 (2010); and Mao et al., *Hum. Gene Therapy*, 22: 1525-1535 (2011)).

The inventive AAV vector comprises a nucleic acid sequence encoding an antibody that binds to nicotine or a nicotine analog, or an antigen-binding fragment thereof (also referred to herein as an "anti-nicotine antibody"). "Nucleic acid sequence" is intended to encompass a polymer of DNA or RNA, i.e., a polynucleotide, which can be single-stranded or double-stranded and which can contain non-natural or altered nucleotides. The terms "nucleic acid" and "polynucleotide" as used herein refer to a polymeric form of nucleotides of any length, either ribonucleotides (RNA) or deoxyribonucleotides (DNA). These terms refer to the primary structure of the molecule, and thus include double- and single-stranded DNA, and double- and single-stranded RNA. The terms include, as equivalents, analogs of either RNA or DNA made from nucleotide analogs and modified polynucleotides such as, though not limited to, methylated and/or capped polynucleotides.

One of ordinary skill in the art will appreciate that an antibody consists of four polypeptides: two identical copies of a heavy (H) chain polypeptide and two copies of a light (L) chain polypeptide. Each of the heavy chains contains one N-terminal variable ($V_H$) region and three C-terminal constant ($C_H1$, $C_H2$ and $C_H3$) regions, and each light chain contains one N-terminal variable ($V_L$) region and one C-terminal constant ($C_L$) region. The variable regions of each pair of light and heavy chains form the antigen binding site of an antibody. The inventive AAV vector can comprise one or more nucleic acid sequences, each of which encodes one or more of the heavy and/or light chain polypeptides of an anti-nicotine antibody. In this respect, the inventive AAV vector can comprise a single nucleic acid sequence that encodes the two heavy chain polypeptides and the two light chain polypeptides of an anti-nicotine antibody. Alternatively, the inventive AAV vector can comprise a first nucleic acid sequence that encodes both heavy chain polypeptides of an anti-nicotine antibody, and a second nucleic acid sequence that encodes both light chain polypeptides of an anti-nicotine antibody. In yet another embodiment, the inventive AAV vector can comprise a first nucleic acid sequence encoding a first heavy chain polypeptide of an anti-nicotine antibody, a second nucleic acid sequence encoding a second heavy chain polypeptide of an anti-nicotine antibody, a third nucleic acid sequence encoding a first light chain polypeptide of an anti-nicotine antibody, and a fourth nucleic acid sequence encoding a second light chain polypeptide of an anti-nicotine antibody.

In another embodiment, the AAV vector can comprise a nucleic acid sequence that encodes an antigen-binding fragment (also referred to as an "antibody fragment") of an anti-nicotine antibody. The term "antigen-binding fragment" refers to one or more fragments of an antibody that retain the ability to specifically bind to an antigen (e.g., nicotine or a nicotine analog) (see, generally, Holliger et al., *Nat. Biotech.*, 23(9): 1126-1129 (2005)). Examples of antigen-binding fragments include but are not limited to (i) a Fab fragment, which is a monovalent fragment consisting of the $V_L$, $V_H$, $C_L$, and $C_H1$ domains; (ii) a F(ab')$_2$ fragment, which is a bivalent fragment comprising two Fab fragments linked by a disulfide bridge at the hinge region; and (iii) a Fv fragment consisting of the $V_L$ and $V_H$ domains of a single arm of an antibody. In one embodiment, the AAV vector can comprise a nucleic acid sequence encoding a Fab fragment of an anti-nicotine antibody.

The nucleic acid sequence can encode an antibody that binds to nicotine itself or to any nicotine analog known in the art. Suitable nicotine analogs include any nicotine analog that induces an immune response in a mammal (humoral or cell-mediated). Nicotine analogs are known in the art (see, e.g., Cerny et al., *Onkologie*, 25: 406-411 (2002); Lindblom et al., *Respiration*, 69: 254-260 (2002); de Villiers et al., *Respiration*, 69: 247-253 (2002); Tuncok et al., *Exp. Clin. Psychopharmacol.*, 9: 228-234 (2001); Hieda et al., *Int. J. Immunopharmacol.*, 22: 809-819 (2000); Pentel et al., *Pharmacol. Biochem. Behav.*, 65: 191-198 (2000); Isomura et al., *J. Org. Chem.*, 66: 4115-4121 (2001); and Meijler et al., *J. Am. Chem. Soc.*, 125: 7164-7165 (2003)). For example, the nicotine analog can be N-succinyl-6-amino-(+/−)-nicotine (Castro et al., *Biochem. Biophys. Res. Commun.*, 67: 583-589 (1975)), 6-(sigma-aminocapramido)-(+/−)-nicotine (Noguchi et al., *Biochem. Biophys. Res. Comm.*, 83: 83-86 (1978)), O-succinyl-3'-hydroxymethyl-nicotine (Langone et al., *Biochemistry*, 12: 5025-5030 (1973); and *Meth. Enzymol.*, 84: 628-640 (1982)), or 3'-(hydroxymethyl)-nicotine hemisuccinate (Langone et al., supra; and Abad et al., *Anal. Chem.*, 65: 3227-3231 (1993)). Additional examples of nicotine analogs suitable for use in the invention are described in U.S. Pat. Nos. 6,232,082 and 6,932,971.

In one embodiment, the nucleic acid sequence can encode the high-affinity, nicotine-binding monoclonal antibody NIC9D9 (see, e.g., Carrera et al., *Bioorg. Med. Chem.*, 12: 563-570 (2004) and Isomura et al., *J. Org. Chem.*, 66: 4115-4121 (2001)). In this respect, the inventive AAV vector can comprise a nucleic acid sequence encoding full-length heavy and light chain polypeptides of NIC9D9. Amino acid sequences of the heavy and light chain polypeptides of NIC9D9 are known in the art and comprise the amino acid sequences of SEQ ID NO: 2 and SEQ ID NO: 3, respectively. In a preferred embodiment, the inventive AAV vector comprises a nucleic acid sequence encoding a Fab fragment of the NIC9D9 monoclonal antibody. For example, the inventive AAV vector can comprise the nucleic acid sequence of SEQ ID NO: 1.

An antibody, or antigen-binding fragment thereof, can be obtained by any means, including via in vitro sources (e.g., a hybridoma or a cell line producing an antibody recombinantly) and in vivo sources (e.g., rodents). Methods for generating antibodies are known in the art and are described in, for example, Köhler and Milstein, *Eur. J. Immunol.*, 5: 511-519 (1976); Harlow and Lane (eds.), *Antibodies: A Laboratory Manual*, CSH Press (1988); and C. A. Janeway et al. (eds.), *Immunobiology*, 5th Ed., Garland Publishing, New York, N.Y. (2001)). In certain embodiments, a human antibody or a chimeric antibody can be generated using a transgenic animal (e.g., a mouse) wherein one or more endogenous immunoglobulin genes are replaced with one or more human immunoglobulin genes. Examples of transgenic mice wherein endogenous antibody genes are effectively replaced with human antibody genes include, but are not limited to, the HUMAB-MOUSE™, the Kirin TC MOUSE™, and the KM-MOUSET™ (see, e.g., Lonberg, *Nat. Biotechnol.*, 23(9): 1117-25 (2005), and Lonberg, *Handb. Exp. Pharmacol.*, 181: 69-97 (2008)).

The nucleic acid sequence encoding the nicotine-binding antibody, or an antigen-binding fragment thereof, can be generated using methods known in the art. For example, nucleic acid sequences, polypeptides, and proteins can be recombinantly produced using standard recombinant DNA methodology (see, e.g., Sambrook et al., *Molecular Cloning: A Laboratory Manual*, 3$^{rd}$ ed., Cold Spring Harbor Press, Cold Spring Harbor, N.Y., 2001; and Ausubel et al., *Current Protocols in Molecular Biology*, Greene Publishing Associates and John Wiley & Sons, NY, 1994). Further, a synthetically produced nucleic acid sequence encoding an anti-nicotine antibody, or an antigen-binding fragment thereof, can be isolated and/or purified from a source, such as a bacterium, an insect, or a mammal, e.g., a rat, a human, etc. Methods of isolation and purification are well-known in the art. Alternatively, the nucleic acid sequences described herein can be commercially synthesized. In this respect, the nucleic acid sequence can be synthetic, recombinant, isolated, and/or purified.

In addition to the nucleic acid sequence encoding an anti-nicotine antibody, or an antigen-binding fragment thereof, the AAV vector preferably comprises expression control sequences, such as promoters, enhancers, polyadenylation signals, transcription terminators, internal ribosome entry sites (IRES), and the like, that provide for the expression of the nucleic acid sequence in a host cell. Exemplary expression control sequences are known in the art and described in, for example, Goeddel, *Gene Expression Technology: Methods in Enzymology*, Vol. 185, Academic Press, San Diego, Calif. (1990).

A large number of promoters, including constitutive, inducible, and repressible promoters, from a variety of different sources are well known in the art. Representative sources of promoters include for example, virus, mammal, insect, plant, yeast, and bacteria, and suitable promoters from these sources are readily available, or can be made synthetically, based on sequences publicly available, for example, from depositories such as the ATCC as well as other commercial or individual sources. Promoters can be unidirectional (i.e., initiate transcription in one direction) or bi-directional (i.e., initiate transcription in either a 3' or 5' direction). Non-limiting examples of promoters include, for example, the T7 bacterial expression system, pBAD (araA) bacterial expression system, the cytomegalovirus (CMV) promoter, the SV40 promoter, and the RSV promoter. Inducible promoters include, for example, the Tet system (U.S. Pat. Nos. 5,464,758 and 5,814,618), the Ecdysone inducible system (No et al., *Proc. Natl. Acad. Sci.*, 93: 3346-3351 (1996)), the T-REX™ system (Invitrogen, Carlsbad, Calif.), LACSWITCH™ System (Stratagene, San Diego, Calif.), and the Cre-ERT tamoxifen inducible recombinase system (Indra et al., *Nuc. Acid. Res.*, 27: 4324-4327 (1999); *Nuc. Acid. Res.*, 28: e99 (2000); U.S. Pat. No. 7,112,715; and Kramer & Fussenegger, *Methods Mol. Biol.*, 308: 123-144 (2005)).

The term "enhancer" as used herein, refers to a DNA sequence that increases transcription of, for example, a nucleic acid sequence to which it is operably linked. Enhancers can be located many kilobases away from the coding region of the nucleic acid sequence and can mediate the binding of regulatory factors, patterns of DNA methylation, or changes in DNA structure. A large number of enhancers from a variety of different sources are well known in the art and are available as or within cloned polynucleotides (from, e.g., depositories such as the ATCC as well as other commercial or individual sources). A number of polynucleotides comprising promoters (such as the commonly-used CMV promoter) also comprise enhancer sequences. Enhancers can be located upstream, within, or downstream of coding sequences. Preferably, the nucleic acid sequence encoding the anti-nicotine antibody, or an antigen-binding fragment thereof, is operably linked to a CMV enhancer/chicken β-actin promoter (also referred to as a "CAG promoter") (see, e.g., Niwa et al., *Gene*, 108: 193-199 (1991); Daly et al., *Proc. Natl. Acad. Sci. U.S.A.*, 96: 2296-2300 (1999); and Sondhi et al., *Mol. Ther.*, 15: 481-491 (2007)).

The invention provides a composition comprising, consisting essentially of, or consisting of the above-described AAV vector and a pharmaceutically acceptable (e.g. physiologically acceptable) carrier. When the composition consists essentially of the inventive AAV vector and a pharmaceutically acceptable carrier, additional components can be included that do not materially affect the composition (e.g., adjuvants, buffers, stabilizers, anti-inflammatory agents, solubilizers, preservatives, etc.). When the composition consists of the inventive AAV vector and the pharmaceutically acceptable carrier, the composition does not comprise any additional components. Any suitable carrier can be used within the context of the invention, and such carriers are well known in the art. The choice of carrier will be determined, in part, by the particular site to which the composition may be administered and the particular method used to administer the composition. The composition optionally can be sterile with the exception of the AAV vector described herein. The composition can be frozen or lyophilized for storage and reconstituted in a suitable sterile carrier prior to use. The compositions can be generated in accordance with conventional techniques described in, e.g., *Remington: The Science and Practice of Pharmacy*, 21st Edition, Lippincott Williams & Wilkins, Philadelphia, Pa. (2001).

Suitable formulations for the composition include aqueous and non-aqueous solutions, isotonic sterile solutions, which can contain anti-oxidants, buffers, and bacteriostats, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, immediately prior to use. Extemporaneous solutions and suspensions can be prepared from sterile powders, granules, and tablets of the kind previously described. Preferably, the carrier is a buffered saline solution. More preferably, the inventive AAV vector is administered in a composition formulated to protect the inventive AAV vector from damage prior to administration. For example, the composition can be formulated to reduce loss of the AAV vector on devices used to prepare, store, or administer the AAV vector, such as glassware, syringes, or needles. The composition can be formulated to decrease the light sensitivity and/or temperature sensitivity of the AAV vector. To this end, the composition preferably comprises a pharmaceutically acceptable liquid carrier, such as, for example, those described above, and a stabilizing agent selected from the group consisting of polysorbate 80, L-arginine, polyvinylpyrrolidone, trehalose, and combinations thereof. Use of such a composition will extend the shelf life of the AAV vector, facilitate administration, and increase the efficiency of the inventive method. Formulations for AAV vector-containing compositions are further described in, for example, Wright et al., *Curr. Opin. Drug Discov. Devel.*, 6(2): 174-178 (2003) and Wright et al., *Molecular Therapy*, 12: 171-178 (2005))

The composition also can be formulated to enhance transduction efficiency. In addition, one of ordinary skill in the art will appreciate that the inventive AAV vector can be present in a composition with other therapeutic or biologically-active agents. For example, factors that control inflammation, such as ibuprofen or steroids, can be part of the composition to reduce swelling and inflammation associated with in vivo administration of the AAV vector. Immune system stimulators or adjuvants, e.g., interleukins, lipopolysaccharide, and double-stranded RNA, can be administered to enhance or modify the anti-nicotine immune response. Antibiotics, i.e., microbicides and fungicides, can be present to treat existing infection and/or reduce the risk of future infection, such as infection associated with gene transfer procedures.

The invention provides a method of inducing an immune response against nicotine in a mammal, which comprises administering the composition comprising the inventive AAV vector to the mammal, whereupon the nucleic acid is expressed to product the antibody that binds to nicotine or a nicotine analog and induce an immune response against nicotine in the mammal. In a preferred embodiment, the mammal is a human that currently smokes (i.e., a smoker), a human that has previously smoked but is no longer smoking, or a human that has never smoked. The AAV vector preferably is administered to a mammal, whereupon an immune response against nicotine is induced. Since the inventive AAV vector comprises a nucleic acid sequence encoding an antibody, the immune response desirably is a humoral immune response. Ideally, the immune response provides a clinical benefit upon exposure to the antigen. A "clinical benefit" can be, for example, a reduction in the physiological effects of nicotine, a reduction in the reward or pleasure associated with use of nicotine, a reduction in the likelihood of regaining an addiction to nicotine, or a prophylactic effect (i.e., smoking prevention). However, a clinical benefit is not required in the context of the invention. The inventive method further can be used for antibody production and harvesting. For example, the inventive method can be used to produce antibodies for diagnostic purposes (e.g., to detect the presence of nicotine or a nicotine analog in blood).

Any route of administration can be used to deliver the composition to the mammal. Indeed, although more than one route can be used to administer the composition, a particular route can provide a more immediate and more effective reaction than another route. Preferably, the composition is administered via intramuscular injection. A dose of composition also can be applied or instilled into body cavities, absorbed through the skin (e.g., via a transdermal patch), inhaled, ingested, topically applied to tissue, or administered parenterally via, for instance, intravenous, peritoneal, or intraarterial administration.

The composition can be administered in or on a device that allows controlled or sustained release, such as a sponge, biocompatible meshwork, mechanical reservoir, or mechanical implant. Implants (see, e.g., U.S. Pat. No. 5,443,505), devices (see, e.g., U.S. Pat. No. 4,863,457), such as an implantable device, e.g., a mechanical reservoir or an implant or a device comprised of a polymeric composition, are particularly useful for administration of the AAV vector. The composition also can be administered in the form of sustained-release formulations (see, e.g., U.S. Pat. No. 5,378,475) comprising, for example, gel foam, hyaluronic acid, gelatin, chondroitin sulfate, a polyphosphoester, such as bis-2-hydroxyethyl-terephthalate (BHET), and/or a polylactic-glycolic acid.

The dose of the AAV vector in the composition administered to the mammal will depend on a number of factors, including the size (mass) of the mammal, the extent of any side-effects, the particular route of administration, and the like. Preferably, the inventive method comprises administering a "therapeutically effective amount" of the composition comprising the inventive AAV vector described herein. A "therapeutically effective amount" refers to an amount effective, at dosages and for periods of time necessary, to achieve a desired therapeutic result. The therapeutically effective amount may vary according to factors such as the degree of nicotine addiction, age, sex, and weight of the individual, and the ability of the AAV vector to elicit a desired response in the individual. In another embodiment, the inventive method can comprise administering a "prophylactically effective amount" of the composition comprising the inventive AAV vector. A "prophylactically effective amount" refers to an amount effective, at dosages and for periods of time necessary, to achieve a desired prophylactic result (e.g., prevention of nicotine addiction). The dose of AAV vector in the composition required to achieve a particular therapeutic or prophylactic effect (i.e., prevention or treatment of nicotine addiction) typically is administered in units of vector genome copies per cell (gc/cell) or vector genome copies/per kilogram of body weight (gc/kg). One of ordinary skill in the art can readily determine an appropriate AAV vector dose range to treat a patient having a particular disease or disorder, such as nicotine addiction, based on these and other factors that are well known in the art.

In a preferred embodiment of the invention, the composition is administered once to the mammal. It is believed that a single administration of the composition will result in persistent expression of the anti-nicotine antibody in the mammal with minimal side effects. However, in certain cases, it may be appropriate to administer the composition multiple times during a therapeutic period and/or employ multiple administration routes, e.g., intramuscular and subcutaneous, to ensure sufficient exposure of cells to the composition. For example, the composition may be administered to the mammal two or more times (e.g., 2, 3, 4, 5, 6, 6, 8, 9, or 10 or more times) during a therapeutic period.

The composition can be administered in conjunction with counseling and/or one or more additional agents that prevent or treat nicotine addiction. For example, the additional agent can be, for example, an anti-depressant, a nicotine receptor modulator, a cannabinoid receptor antagonist, an opioid receptor antagonist, a monoamine oxidase inhibitor, an anxiolytic, or any combination of these agents. Preferably, the additional agent is an anti-depressant selected from the group consisting of bupropion, doxepin, desipramine, clomipramine, imipramine, nortriptyline, amitriptyline, protriptyline, trimipramine, fluoxetine, fluvoxamine, paroxetine, sertraline, phenelzine, tranylcypromine, amoxapine, maprotiline, trazodone, venlafaxine, mirtazapine, and pharmaceutically active salts or optical isomers thereof.

The following examples further illustrate the invention but, of course, should not be construed as in any way limiting its scope.

Example 1

This example demonstrates the generation of an AAV vector comprising a nucleic acid sequence encoding an anti-nicotine antibody fragment.

AAVrh.10antiNic.Mab vector (also referred to herein as "AAVantiNic") is an AAV vector based on the non-human primate-derived rh.10 capsid pseudotyped with AAV2 inverted terminal repeats surrounding the anti-nicotine antibody expression cassette (see FIG. 1A). The expression cassette contains a cytomegalovirus (CMV) enhancer-chicken-β-actin promoter, a nucleic acid sequence encoding an amino acid sequence of SEQ ID NO: 2, corresponding to the heavy chain polypeptide of the anti-nicotine monoclonal antibody NIC9D9, a 4-amino-acid furin cleavage site and the 24-amino-acid self-cleaving 2A peptide, a nucleic acid sequence encoding an amino acid sequence of SEQ ID NO: 3, which corresponds to the NIC9D9 light chain polypeptide, and the rabbit β-globin polyadenylation signal (see, e.g., Isomura et al., supra; Fang et al., *Nat. Biotechnol.*, 23: 584-590 (2005); Mao et al., *Hum. Gene Ther.*, 22(5): 567-575 (2011); and Niwa et al., *Gene*, 108: 193-199 (1991)). The cDNA sequence of the NIC9D9 antibody heavy chain (IgG1) and light chain (K chain) were cloned from the mouse hybridoma NIC9D9 (Niwa et al., supra), using RNA ligase-mediated rapid amplification of cDNA ends (GENERACER kit, Invitrogen, Carlsbad, Calif.) with mouse immunoglobulin gene-specific primers. The negative control vector AAVrh.10antiPA.Mab (referred to as "AAVcontrol") encodes an irrelevant antibody directed against anthrax protective antigen.

AAVantiNic was produced by PolyFect-mediated (Qiagen, Germantown, Md.) cotransfection into HEK 293 cells (American Type Culture Collection) of three plasmids: pAAVaNIC9D9 (600 mg), pAAV442 (600 mg), and pAdDF6 (1.2 mg). pAAVNIC9D9 is an expression plasmid containing (5' to 3') the AAV2 5' ITR including packaging signal (ψ), the anti-mouse NIC9D9 antibody expression cassette described above, and the AAV2 3' ITR. pAAV44.2 is a packaging plasmid that provides the AAV Rep proteins derived from AAV2 needed for vector replication and the AAVrh.10 viral structural (Cap) proteins VP1, 2, and 3, which define the serotype of the AAV vector. pAdDF6 is an adenovirus helper plasmid that provides adenovirus helper functions of E2, E4, and VA RNA (Xiao et al., *J. Virol.*, 72, 2224-2232 (1998)). At 72 hours after transfection, the cells were harvested, and a crude viral lysate was prepared by four cycles of freeze/thaw and clarified by centrifugation. AAVantiNic was purified by iodixanol gradient and QHP anion exchange chromatography. The purified AAVantiNic was concentrated with an Amicon Ultra-15 100K centrifugal filter device (Millipore, Billerica, Mass.) and stored in PBS (pH 7.4) at −80° C. The control vector was produced using the same method but substituting pAAVantiPA.Mab for pAAVantiNic.

Vector genome titers were determined by quantitative TaqMan real-time PCR analysis using a cytomegalovirus promoter-specific primer-probe set (Applied Biosystems, Foster City, Calif.).

To assess AAVantiNic-directed expression of the monoclonal antibody in vitro, HEK 293 cells were infected with AAVantiNic at $2 \times 10^5$ genome copies (gc) per cell (or mock infected), harvested at 72 hours post-infection, and purified using protein G sepharose. All media were evaluated for the expression of the anti-nicotine antibody by coomassie blue stain and Western analysis (Mao et al., supra) using a sheep anti-mouse IgG heavy chain and light chain secondary antibody (Sigma, Saint Louis, Mo.) and enhanced chemiluminescence reagent (Amersham, Piscataway, N.J.).

The results of these experiments are set forth in FIGS. 1B and 1C. HEK 293 cells infected with the AAVantiNic secreted IgG antibody as demonstrated by coomassie blue stain SDS-PAGE and Western analysis. Mock-infected cells showed no IgG-related bands.

The results of this example demonstrate the production of the inventive AAV vector and that the encoded anti-nicotine antibody is expressed and secreted from cells in vitro.

Example 2

This example demonstrates a method of inducing an anti-nicotine immune response in a mammal using the inventive AAV vector.

To assess the ability of AAVantiNic to express and maintain high levels of anti-nicotine antibody in serum, C57Bl/6 mice were administered AAVantiNic at $10^9$, $10^{10}$ or $10^{11}$ genome copies (gc) by intravenous route. All animal studies were conducted under protocols reviewed and approved by the Weill Cornell Institutional Animal Care and Use Committee. Male C57Bl/6 mice, 4 to 6 weeks old (Taconic, Germantown, N.Y.) were housed under pathogen-free conditions. Experiments were initiated at 7 to 9 weeks of age. Blood was collected from the transected tail vein, allowed to clot, centrifuged at 10,000 g for 20 minutes, and serum was stored at −20° C.

Antibody levels in serum from treated mice were analyzed using an ELISA assay. Specifically, wells of flat bottomed 96-well EIA/RIA plates (Corning, N.Y., N.Y.) were coated with 100 µl of 1 mg/ml bovine serum albumin conjugated with AM1, which is a trans-3'-(hydroxymethyl) nicotine-derived nicotine hapten (ratio of 2:1) (see Moreno et al., *Mol. Pharm.*, 7: 431-441 (2010)) in carbonate-buffer overnight at 4° C., washed with 0.05% Tween 20 in PBS (PBS-Tween), and blocked with 5% dry milk in PBS for 30 minutes at 23° C. Serial dilutions of sera were incubated for 90 minutes at 23° C. The plates were washed four times with PBS-Tween and 100 ml of 1:2000 diluted goat anti-mouse IgG conjugated to horseradish peroxidase (Santa Cruz Biotechnology, Inc., Santa Cruz, Calif.) in 1% dry milk in PBS and incubated for 90 minutes at 23° C. After four wash steps, peroxidase substrate (100 ml per well; Bio-Rad, Hercules, Calif.) was added to each well and incubated for 15 minutes at 23° C., and the reaction was stopped with the addition of 2% oxalic acid (100 ml per well). Absorbance was measured at 415 nm.

Anti-nicotine antibody titers were calculated by interpolation of the log(OD)-log(dilution) with a cutoff value equal to 2-fold the absorbance of background and converted to µg/ml based on the NIC9D9 antibody standard ELISA titer. NIC9D9 antibody was quantified by the bicinchoninic acid assay (Pierce Biotechnology, Rockford, Ill.). To demonstrate that the antibody expressed by AAVantiNic was nicotine-specific, inhibition of binding of sera from AAVantiNic-immunized mice to bovine serum albumin BSA-AM1 nicotine hapten by ELISA was performed in the presence of increasing concentrations of nicotine, and nicotine metabolites nornicotine or cotinine, from 0.1 nM to 0.1 mM. Affinity of the expressed antibody from sera from AAVantiNic-treated mice was evaluated by a radioimmunoassay, using [$^3$H]nicotine (10 nm) with increasing concentrations of nonlabeled nicotine (1 to 300 nm) as the unlabeled competitor (see Müller, *Methods Enzymol.*, 92: 589-601 (1983)).

The results of the ELISA analysis are set forth in FIGS. 2A-2C. The $10^{11}$ gc dose of AAVantiNic resulted in the highest level of anti-nicotine antibody expression, with a mean titer of 1.1±0.2 mg/ml at week 9 (FIG. 2A). Assessment of sera of AAVantiNic-vaccinated mice from 0 to 18 weeks showed high levels of expression of anti-nicotine antibody, reaching 0.9±0.1 mg/ml by 4 weeks and remaining high at 1.3±0.1 mg/ml at 18 weeks (FIG. 2B). The expressed anti-nicotine antibody had a higher specificity for nicotine compared to its metabolites nornicotine and cotinine (FIG. 2C). The Kd for nicotine was 43±20 nmol/l (FIG. 2D).

The results of this example demonstrate that high levels of anti-nicotine antibody can be produced and maintained by vaccinating mice with the inventive AAV vector.

Example 3

This example describes the pharmacokinetics of nicotine in mice vaccinated with the inventive AAV vector.

To test if immunization with AAVantiNic results in sufficient levels of anti-nicotine antibodies to shield the brain from systemically administered nicotine, AAVantiNic-treated mice were challenged intravenously with radio-labeled nicotine (see, e.g., Benowitz et al., *Clin. Pharmacol. Ther.*, 35: 499-504 (1984) and Hieda et al., *J. Pharmacol. Exp. Ther.*, 283: 1076-1081 (1997)). Untreated or AAVantiNic-administered mice were anesthetized by intraperitoneal injection of ketamine (100 mg/kg) and xylazine (10 mg/kg) three minutes prior to intravenous administration of 0.8 µg nicotine (a dose equivalent to 2 cigarettes in a human) containing 1.0 µCi [$^3$H]nicotine (see Benowitz et al., supra, and Hieda et al., supra). One minute later, mice were sacrificed, and the brain and blood were collected separately. Brain tissue was homogenized in PBS, and 300 µA of brain homogenate and 50 µl of serum were separately added to 5 ml of liquid scintillant (ULTIMA GOLD™, PerkinElmer, Waltham, Mass.), which were assayed in triplicate for tritium and normalized with a standard quenching curve. For the blood compartment, nicotine was normalized to serum volume (ng/ml), and the brain was normalized to brain wet weight (ng/g).

The results of this experiment are shown in FIGS. 3A and 3B. At one minute post-nicotine administration, total serum nicotine levels in AAVantiNic-treated mice (516 ng/ml) were 7.1-fold higher compared to non-immunized mice (71.7 ng/ml) ($p<10^{-5}$). In the AAVantiNic-treated mice, 83% of the serum nicotine was IgG-bound. Conversely, nicotine levels in the brain of immunized mice (12.2 ng/g brain) were reduced by 85% compared to non-immunized mice (79.2 ng/g brain), demonstrating a 46-fold reduction in the ratio of brain to blood nicotine level in the passively immunized mice ($p<10^{-5}$).

The results of this example demonstrate that vaccination with the inventive AAV vector prevents nicotine from entering the brain of treated mice.

Example 4

This example demonstrates that the inventive AAV vector suppresses the cardiovascular effects of nicotine.

AAVantiNic or control vector were administered to mice as described above. Seven weeks following vector administration, mice were implanted with radio-telemeters (Data Sciences International, St. Paul, Minn., PA-C10 model) as described in Butz et al., *Physiol Genomics*, 5: 89-97 (2001). One week following telemeter implantation, baseline measurements of mean arterial blood pressure (MAP) and heart rate (HR) were collected for 30 minutes in conscious mice. Subsequently, nicotine (25.0 µg, 1.0 mg/kg) or PBS was administered subcutaneously, and cardiovascular parameters were continuously recorded for the following 180 minutes using the DSI Dataquest A.R.T. system (Data Sciences International, St. Paul, Minn.).

Systemic administration of nicotine resulted in robust changes in cardiovascular parameters in mice immunized with the control vector, as shown in FIGS. 4A and 4B. In particular, nicotine caused a 37% reduction in MAP and a 46% reduction in HR in the control mice within 25 minutes. In contrast, these MAP and HR responses were abolished in AAVantiNic-immunized mice following nicotine challenge. There was no change in MAP or HR in immunized mice administered PBS as a control.

The results of this example demonstrate that vaccination with the inventive AAV vector inhibits adverse cardiovascular effects of nicotine.

Example 5

This example demonstrates that the inventive AAV vector prevents nicotine-induced suppression of locomotion in animals.

AAVantiNic was administered to mice as described above, and naïve mice served as controls. Four weeks following vector administration, locomotor behavior was recorded using infrared beam-equipped activity chambers (20×20 cm chamber, AccuScan Instruments, Columbus, Ohio). Mice were allowed to habituate to the room for one hour prior to each test. Mice were placed in the chamber for 15 minutes to record pre-challenge behavior. Animals were then removed, injected with PBS or nicotine (12.5 µg, 0.5 mg/kg) subcutaneously, and returned to the chamber for 15 additional minutes. To test the efficacy of AAVantiNic, mice were repeatedly challenged with nicotine over a three-week period for a total of ten nicotine challenges. Locomotor activity was collected as ambulatory distance traveled and vertical movement.

The results of these tests are shown in FIGS. 5A-5C. Non-immunized mice showed a marked nicotine-dependent decrease in locomotor activity on all days tested, while AAVantiNic-vaccinated mice had the same ambulatory activity profile as non-immunized mice administered saline. At day 18 of the nicotine challenges (7 weeks post administration of AAVantiNic), assessment of the cumulative distance traveled demonstrated that non-immunized mice had a nicotine-induced suppression of ambulatory activity (2.15±0.30 m over 15 minutes, p<0.003) compared to saline-injected control mice, whereas AAVantiNic-treated mice did not show nicotine-induced hypolocomotion, traveling 6.38±1.20 m, which is similar to mice administered saline which traveled 5.00±0.75 m (p>0.6; FIG. 5B). Assessment of the cumulative vertical activity profile showed the same differences, as control mice receiving nicotine displayed 16.8±3.0 seconds of vertical activity (over 15 minutes) ($p<10^{-5}$ compared to saline injected, non-immunized mice), and immunized mice receiving nicotine exhibited 180.2±26.7 seconds of vertical activity (over 15 minutes), which was similar to mice administered saline instead of nicotine (200.6±36.6 sec, p>0.9; FIG. 5C).

The results of this example demonstrate that vaccination with the inventive AAV vector inhibits adverse locomotor effects of nicotine.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An adeno-associated virus (AAV) vector comprising a nucleic acid sequence which encodes an antibody that binds nicotine or a nicotine analog, or an antigen-binding fragment thereof, wherein the antibody comprises a heavy chain polypeptide comprising the amino acid sequence of SEQ ID NO: 2 and a light chain polypeptide comprising the amino acid sequence of SEQ ID NO: 3.

2. The AAV vector of claim 1, wherein the nucleic acid sequence encodes an antibody fragment.

3. The AAV vector of claim 2, wherein the antibody fragment is a F(ab')2, a Fab', a Fab, a Fv, a say, a dsFv, a dAb, or a single chain binding polypeptide.

4. The AAV vector of claim 3, wherein the antibody fragment is a Fab.

5. The AAV vector of claim 1, wherein the nucleic acid sequence comprises SEQ ID NO: 1.

6. The AAV vector of claim 1, which is generated using a non-human adeno-associated virus.

7. The AAV vector of claim 1, which is generated using a rhesus macaque adeno-associated virus.

8. A composition comprising the AAV vector of claim 1 and a pharmaceutically-acceptable carrier.

9. A method of inducing an immune response against nicotine in a mammal, which comprises administering the composition of claim 8 to the mammal, whereupon the nucleic acid is expressed to produce the antibody and induce an immune response against nicotine in the mammal.

10. The method of claim 9, wherein the composition is administered to the mammal once during a therapeutic period.

11. The method of claim 9, wherein the composition is administered to the mammal two or more times during a therapeutic period.

12. The method of claim 9, wherein the mammal is a human.

\* \* \* \* \*

SEQUENCE LISTING

```
<160> NUMBER OF SEQ ID NOS: 3

<210> SEQ ID NO 1
<211> LENGTH: 2200
<212> TYPE: DNA
<213> ORGANISM: Artificial Sequence
<220> FEATURE:
<223> OTHER INFORMATION: Synthetic

<400> SEQUENCE: 1
```

-continued

| | |
|---|---|
| gccaccatgg aatgaccctg gtctttctc ttcctcctgt cagtgcctgc aggtgtccac | 60 |
| tcccagtttc agctgcagca gtctggaact gagctgatga agcctggggc ctcagtgaag | 120 |
| atatcctgca aggcttctgc ctacacattc aatacctact ggatagagtg gattaaacag | 180 |
| aggcctggac ttggccttga gtggattgga gaaattttac ctggaagtgg aagtactcac | 240 |
| tacaatgaga attcaaggc caaggccaca ttcactgcag atacatcctc caacacagcc | 300 |
| ttcatgcaac tcaacagcct gacatctgag gactctgccg tctattactg tgcaacgggt | 360 |
| gggtcctatg gtaactacga ttacttcgat gtctggggcg ctgggaccac ggtcaccgtc | 420 |
| tcctcagcca aaacgacacc cccatctgtc tatccactgg ccctggatc tgctgcccaa | 480 |
| actaactcca tggtgaccct gggatgcctg gtcaagggct atttccctga ccagtgaca | 540 |
| gtgacctgga ctctggatcc ctgtccagc ggtgtgcaca ccttcccagc tgtcctgcag | 600 |
| tctgacctct acactctgag cagctcagtg actgtcccct ccagcacctg gcccagcgag | 660 |
| accgtcacct gcaacgttgc ccaccccggcc agcagcacca aggtggacaa gaaaattgtg | 720 |
| cccagggatt gtggttgtaa gccttgcata tgtacagtcc cagaagtatc atctgtcttc | 780 |
| atcttcccc caaagcccaa ggatgtgctc accattactc tgactcctaa ggtcacgtgt | 840 |
| gttgtggtag acatcagcaa ggatgatccc gaggtccagt tcagctggtt tgtagatgat | 900 |
| gtggaggtgc acacagctca gacgcaaccc cgggaggagc agttcaacag cactttccgc | 960 |
| tcagtcagtg aacttcccat catgcaccag gactggctca atggcaagga gttcaaatgc | 1020 |
| agggtcaaca gtgcagcttt ccctgccccc atcgagaaaa ccatctccaa aaccaaaggc | 1080 |
| agaccgaagg ctccacaggt gtacaccatt ccacctccca aggagcagat ggccaaggat | 1140 |
| aaagtcagtc tgacctgcat gataacagac ttcttccctg aagacattac tgtggagtgg | 1200 |
| cagtggaatg ggcagccagc ggagaactac aagaacactc agcccatcat ggacacagat | 1260 |
| ggctcttact tcgtctacag caagctcaat gtgcagaaga gcaactggga ggcaggaaat | 1320 |
| actttcacct gctctgtgtt acatgagggc ctgcacaacc accatactga aaagagcctc | 1380 |
| tcccactctc ctggtaaaag agccaagagg gcacctgtga acagactttt gaattttgac | 1440 |
| cttctcaagt tggcgggaga cgtcgagtcc aaccctgggc ccatgaagtt gcctgttagg | 1500 |
| ctgttggtgc tgatgttctg gattcctgct tccagcagtg atgttgtgat gacccaaagt | 1560 |
| ccactctccc tgcctgtcag tcttggagat cgagccgcca tatcttgcag atctagtcag | 1620 |
| agccttgtaa acagttatgg aatcacctat ttatattggt atttgcagaa gcccggccag | 1680 |
| tctccaaagg tcctgattta caaagtttcc aaacgatttt ctggggtccc agacaggttc | 1740 |
| agtggcagtg gatcagggac agatttcaca ctcaagatca gcagagtgga gactgaggat | 1800 |
| ctgggagttt atttctgctc tcaaacttca cattttcctc ccacgttcgg tgctgggacc | 1860 |
| aagctggagt tgaaacgggc tgatgctgca ccaactgtat ccatcttccc accatccagt | 1920 |
| gagcagttaa catctggagg tgcctcagtc gtgtgcttct tgaacaactt ctaccccaaa | 1980 |
| gacatcaatg tcaagtggaa gattgatggc agtgaacgac aaaatggcgt cctgaacagt | 2040 |
| tggactgatc aggacagcaa agacagcacc tacagcatga gcagcaccct cacgttgacc | 2100 |
| aaggacgagt atgaacgaca taacagctat acctgtgagg ccactcacaa gacatcaact | 2160 |
| tcacccattg tcaagagctt caacaggaat gagtgttaga | 2200 |

<210> SEQ ID NO 2
<211> LENGTH: 464
<212> TYPE: PRT
<213> ORGANISM: Artificial Sequence
<220> FEATURE:
<223> OTHER INFORMATION: Synthetic

<400> SEQUENCE: 2

Met Glu Trp Thr Trp Val Phe Leu Phe Leu Leu Ser Val Pro Ala Gly
1               5                   10                  15

Val His Ser Gln Phe Gln Leu Gln Gln Ser Gly Thr Glu Leu Met Lys
            20                  25                  30

Pro Gly Ala Ser Val Lys Ile Ser Cys Lys Ala Ser Ala Tyr Thr Phe
        35                  40                  45

Asn Thr Tyr Trp Ile Glu Trp Ile Lys Gln Arg Pro Gly Leu Gly Leu
    50                  55                  60

Glu Trp Ile Gly Glu Ile Leu Pro Gly Ser Gly Ser Thr His Tyr Asn
65                  70                  75                  80

Glu Lys Phe Lys Ala Lys Ala Thr Phe Thr Ala Asp Thr Ser Ser Asn
                85                  90                  95

Thr Ala Phe Met Gln Leu Asn Ser Leu Thr Ser Glu Asp Ser Ala Val
            100                 105                 110

Tyr Tyr Cys Ala Thr Gly Gly Ser Tyr Gly Asn Tyr Asp Tyr Phe Asp
        115                 120                 125

Val Trp Gly Ala Gly Thr Thr Val Thr Val Ser Ser Ala Lys Thr Thr
    130                 135                 140

Pro Pro Ser Val Tyr Pro Leu Ala Pro Gly Ser Ala Ala Gln Thr Asn
145                 150                 155                 160

Ser Met Val Thr Leu Gly Cys Leu Val Lys Gly Tyr Phe Pro Glu Pro
                165                 170                 175

Val Thr Val Thr Trp Asn Ser Gly Ser Leu Ser Ser Gly Val His Thr
            180                 185                 190

Phe Pro Ala Val Leu Gln Ser Asp Leu Tyr Thr Leu Ser Ser Ser Val
        195                 200                 205

Thr Val Pro Ser Ser Thr Trp Pro Ser Glu Thr Val Thr Cys Asn Val
    210                 215                 220

Ala His Pro Ala Ser Ser Thr Lys Val Asp Lys Lys Ile Val Pro Arg
225                 230                 235                 240

Asp Cys Gly Cys Lys Pro Cys Ile Cys Thr Val Pro Glu Val Ser Ser
                245                 250                 255

Val Phe Ile Phe Pro Pro Lys Pro Lys Asp Val Leu Thr Ile Thr Leu
            260                 265                 270

Thr Pro Lys Val Thr Cys Val Val Val Asp Ile Ser Lys Asp Asp Pro
        275                 280                 285

Glu Val Gln Phe Ser Trp Phe Val Asp Asp Val Glu Val His Thr Ala
    290                 295                 300

Gln Thr Gln Pro Arg Glu Gln Phe Asn Ser Thr Phe Arg Ser Val
305                 310                 315                 320

Ser Glu Leu Pro Ile Met His Gln Asp Trp Leu Asn Gly Lys Glu Phe
                325                 330                 335

Lys Cys Arg Val Asn Ser Ala Ala Phe Pro Ala Pro Ile Glu Lys Thr
            340                 345                 350

Ile Ser Lys Thr Lys Gly Arg Pro Lys Ala Pro Gln Val Tyr Thr Ile
        355                 360                 365

Pro Pro Pro Lys Glu Gln Met Ala Lys Asp Lys Val Ser Leu Thr Cys
    370                 375                 380

Met Ile Thr Asp Phe Phe Pro Glu Asp Ile Thr Val Glu Trp Gln Trp
385                 390                 395                 400

```
Asn Gly Gln Pro Ala Glu Asn Tyr Lys Asn Thr Gln Pro Ile Met Asp
                405                 410                 415

Thr Asp Gly Ser Tyr Phe Val Tyr Ser Lys Leu Asn Val Gln Lys Ser
            420                 425                 430

Asn Trp Glu Ala Gly Asn Thr Phe Thr Cys Ser Val Leu His Glu Gly
        435                 440                 445

Leu His Asn His His Thr Glu Lys Ser Leu Ser His Ser Pro Gly Lys
    450                 455                 460

<210> SEQ ID NO 3
<211> LENGTH: 238
<212> TYPE: PRT
<213> ORGANISM: Artificial Sequence
<220> FEATURE:
<223> OTHER INFORMATION: Synthetic

<400> SEQUENCE: 3

Met Lys Leu Pro Val Arg Leu Leu Val Leu Met Phe Trp Ile Pro Ala
1               5                   10                  15

Ser Ser Ser Asp Val Val Met Thr Gln Ser Pro Leu Ser Leu Pro Val
            20                  25                  30

Ser Leu Gly Asp Arg Ala Ala Ile Ser Cys Arg Ser Ser Gln Ser Leu
        35                  40                  45

Val Asn Ser Tyr Gly Ile Thr Tyr Leu Tyr Trp Tyr Leu Gln Lys Pro
    50                  55                  60

Gly Gln Ser Pro Lys Val Leu Ile Tyr Lys Val Ser Lys Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Thr Glu Asp Leu Gly Val Tyr Phe Cys
            100                 105                 110

Ser Gln Thr Ser His Phe Pro Pro Thr Phe Gly Ala Gly Thr Lys Leu
        115                 120                 125

Glu Leu Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
    210                 215                 220

Ser Thr Ser Pro Ile Val Lys Ser Phe Asn Arg Asn Glu Cys
225                 230                 235
```